United States Patent [19]

Koga et al.

[11] Patent Number: 5,843,750
[45] Date of Patent: Dec. 1, 1998

[54] SORBITOL KINASE, PROCESS FOR PRODUCING THE SAME, AND SUBSTANTIALLY PURE MICROORGANISM

[75] Inventors: Shinji Koga; Mamoru Takahashi; Kouji Suzuki, all of Shizuoka, Japan

[73] Assignee: Asahi Kasei Kogyo Kabushiki Kaisha, Osaka, Japan

[21] Appl. No.: 809,860

[22] PCT Filed: Sep. 29, 1995

[86] PCT No.: PCT/JP95/01997

§ 371 Date: Apr. 18, 1997

§ 102(e) Date: Apr. 18, 1997

[87] PCT Pub. No.: WO96/11261

PCT Pub. Date: Apr. 18, 1996

[30] Foreign Application Priority Data

Oct. 7, 1994 [JP] Japan ................................. 6-243539
Oct. 13, 1994 [JP] Japan ................................. 6-247419

[51] Int. Cl.$^6$ .............................. C12N 9/12; C12P 21/04
[52] U.S. Cl. ......................................... 435/194; 435/252.1
[58] Field of Search ................................. 435/194, 71.2, 435/252.1

[56] References Cited

PUBLICATIONS

Neubaur et al. (1967) Z. Physiol. Chem., 348(7), "Decomposition of Sorbitol by Bacteria in Rat Feces". pp. 871–876.
Srivastava et al. (1982) Biochim. Biophys. Acta, 717(2), "Formation of Sorbitol 6–phosphate by Bovine and Human Lens Aldose Reductase, Sorbitol Dehydrogenase and Sorbitol Kinase", pp. 210–214.

T. Yaginuma, et al., "Does an enzyme activity capable of phosphorylating sorbitol control utilization of sorbitol at the termination of diapause in eggs of the silkworm, Bombyx Mori?", 1991, pp. 135–141, Comp. Biochem. Physial, vol. 98B, No. 1.
S. K. Srivastava, et al., "Formation of sorbitol 6–phosphata by bovine and human lens aldose reductase, sorbitol dehydrogenase and sorbitol kinase", 1982, pp. 210–213, Biochimica et Biophysica Acta, 717.
N. E. Kelker, et al., "Sorbitol Metabolism in aerobacter aerogenes", Jan., 1971, pp. 160–164, Journal of Bacteriology.

*Primary Examiner*—Jon P. Weber
*Attorney, Agent, or Firm*—Young & Thompson

[57] ABSTRACT

A sorbitol kinase having at least the following physicochemical properties:

(1) Enzymatic action: utilizing mainly ATP, but not substantially phosphoenolpyruvate, as the phosphate donor catalyzing a reaction of generating sorbitol-6-phosphate and ADP from sorbitol and ATP of the formula, sorbitol+ATP→sorbitol-6-phosphate+ADP (2) Substrate specificity: for sorbitol
(3) N-terminal amino acid sequence: containing Met − Arg − Ile − Gly − Ile − Asp − Leu − Gly − Gly − Thr −
− Lys − Thr − Glu − Val − Ile − Ala − Leu − Ser − Glu − Gln (4) Heat stability stable at least up to 60° C. when a 100 mM Tris-HCl buffer (pH 8.5, containing 0.5 U/ml of sorbitol kinase) is heated for 15 minutes at various temperatures and the residual acitvity is measured.

6 Claims, 17 Drawing Sheets

F I G. 1
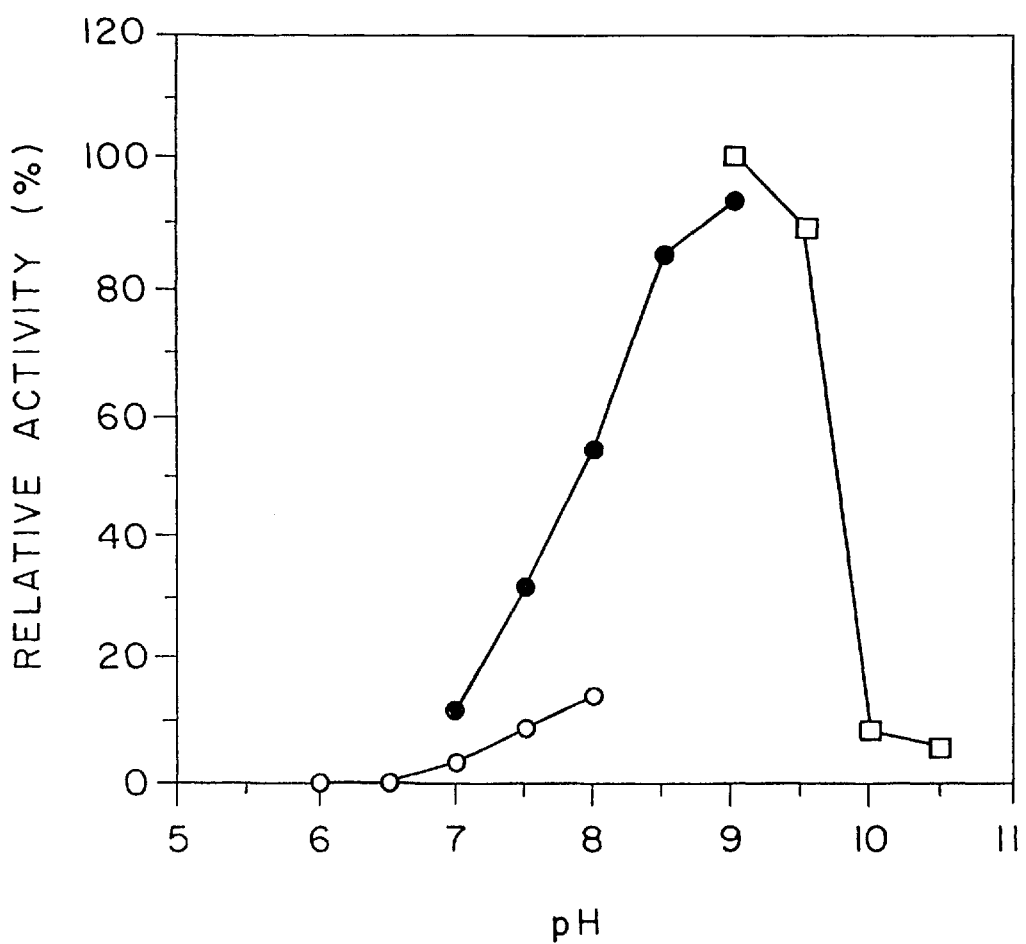

FIG. 9

```
  1  Met Arg Ile Gly Ile Asp Leu Gly Gly Thr Lys Thr Glu Val Ile Ala Leu Ser Glu Gln   20
 21  Gly Glu Gln Leu Phe Arg His Arg Leu Pro Thr Arg Asp Asp Tyr His Gln Thr Ile Ile   40
 41  Glu Thr Ile Ala Arg Leu Val Asp Met Ala Leu Pro Ala Gln Gly Thr Gly Thr Thr Val   60
 61  Gly Met Gly Ile Pro Gly Ser Ile Asp Pro Tyr Thr Gly Val Val Gly Ala Asn Asn Ser   80
 81  Thr Trp Leu Asn Gly Gln Pro Phe Asp Lys Asp Leu Ser Arg Leu Asn Ala Arg Glu Val  100
101  Arg Leu Ala Asn Asp Ala Asn Cys Leu Ala Val Ser Glu Gln Ala Ile Leu Asp Ala Ala  120
121  Gly Ala Gln Thr Val Phe Ala Val Ile Ile Gly Thr Gly Gly Ala Val Gly Asn Ala Leu  140
141  Pro Trp Met Asp Glu Asp Gly Leu Lys Tyr Arg Thr Arg Ala Ala Glu Trp Gly His Leu  160
161  Gln Gly Cys Ile Pro Leu Thr Phe Ile Gly Val Pro Cys Tyr His Asp Pro Cys Gly Leu  180
181  Ser Gly Gln Pro Leu Lys Ser Gly Asn Glu Ile Met Arg Val Ala Lys Ala His Pro Val  200
201  Ala Glu Leu Ala Leu Asp Pro Asp Tyr Glu Gly Gly Met Ser Asn Val Asp Asp Arg Leu  220
221  Asn Ile Leu Asp Pro Asp Val Ile Lys Val Leu Gly Gly Phe Gly Gly Cys Glu Arg Val  240
241  Tyr Ala Thr Val Pro Asn Leu Val Lys Gln Trp Pro Ala Ala Cys Gly Thr Pro Arg Leu  260
261  Ile Arg Lys Cys Arg Ala Ala Ala Pro Arg Pro Ala Ala Pro Ala Arg Gly Ser Gly Pro  280
281  Tyr Ser His Ser Pro Ser Pro Tyr Val Arg Gly Ala Gly                              313
```

FIG. 10

```
GTGCGTATTG GGATTGATTT GGGCGGGCACT AAAACAGAAG TCATCGCACT GAGCGAGCAG   60
GGGGAGCAAC TGTTCCGCCA CCGTCTGCCT ACGCCCGGCG ATGATTATCA CCAGACTATC  120
GAGACGATTG CCCGGCTGGT CGACATGGCT GAGCAGGCGA CAGGGCAGAC CGGCACCGTT  180
GGGATGGGGA TCCCGGGGTC AATCTCGCCC TATACCGGGG TGGTTAAAAA CGCCAACTCC  240
ACCTGGCTCA ACGGTCAGCC TTTTGATAAA GATTTAAGTC AGCGCCTGAA CCGGGAAGTG  300
CGTCTGGCAA ATGACGCCAA CTGTCTGGCC GTCTCCGAAG CCATTGACGG TGCCGCCGCA  360
GGGGCCCAGA CCGTTTTTGC GGTCATTATC GGGACCGGCT GTGGCGCAGG CGTGGCCCTG  420
GGCGGGCGTG CCCATATTGG CGGCAACGGT ACGGGCGGGCG AGTGGGGACA TAACCCCTTG  480
CCGTGGATGG ATGAAGATGA ACTTAAATAC CGCGCCGAGG TGCCGTGCTA TTGCGGCAAG  540
CAGGGCTGTA TTGAGACGTT TATCTCCGGC ACCGGTTTTG CCACCGATTA CCACCGCCTG  600
AGTGGCCAGC CACTCAAGGG GAACGAGATT ATGCGCCGGG TCGGGAACA CGATCCGGTG  660
GCTGAGCTGG CTCTCAGCCG CTATGAAATG CGGCTGGCGA AATCCCTGGC GCACGTGGTG  720
AATATCCTTG ACCCTGACGT GATTGTGCTC GGCGGCGGGA TGAGCAACGT CGACCGTTTA  780
TATGCCACGG TACCGAATCT GGTGAAGCAG TGGGTCTTCG GGGGTGAGTG TGAAACCCCG  840
ATCCGAAAGC GGTGCACGGG GACTCCAGCG GCGTGCGCCG CGCCGCGTGG CTCTGGCCGC  900
TATAGCCATT CTCCCTCTCC CTACGTGAGA GGGGCGGGA                         939
```

SORBITOL KINASE GENE

FIG. 13

AMINO ACID SEQUENCE OF N TERMWAL SITE

| | | | | | | | | | |
|---|---|---|---|---|---|---|---|---|---|
| Met | Arg | Ile | Gly | Ile | Asp | Leu | Gly | Gly | Thr | 10
| Lys | Thr | Glu | Val | Ile | Ala | Leu | Ser | Glu | Gln | 20
| Gly | Glu | Gln | Leu | Phe | Arg | His | Arg | Leu | Pro | 30
| Thr | Pro | Arg | Asp | Asp | Tyr | His | Gln | Thr | Ile | 40
| Glu | Thr | Ile | Ala | Arg | Leu | Val | Asp | Met | Ala | 50
| Glu | Gln | | | | | | | | | 52

FIG. 14

AMINO ACID SEQUENCE OF LYSYLENDOPEPTIDASE SITE K-20

Asn Ala Asn Ser Thr Trp Leu Asn Gly Gln 10
Pro Phe Asp Lys 14

FIG. 15

AMINO ACID SEQUENCE OF LYSYLENDOPEPTIDASE SITE K-27

Xaa Trp Val Phe Gly Gly Glu Xaa Glu Thr 10
Pro Ile Arg Lys 14

FIG. 16

AMINO ACID SEQUENCE OF LYSYLENDOPEPTIDASE SITE K-35

```
Tyr Arg Ala Glu Val Pro Cys Tyr Cys Gly  10
Lys Gln Gly Cys Ile Glu Thr Phe Ile Ser  20
Gly Thr Gly Phe Ala Thr Asp Tyr His Arg  30
Leu Ser                                   32
```

FIG. 17

① NUCLEOTIDE SEQUENCE OF OLIGONUCLEOTIDE PROBE SK1

```
GACGACTACC ACCAAAC       17
   T    T  T    T G
```

② NUCLEOTIDE SEQUENCE OF OLIGONUCLEOTIDE PROBE SK2

```
GACGACTACC ACCAAACCAT    20
   T    T  T    T G  G
```

③ NUCLEOTIDE SEQUENCE OF OLIGONUCLEOTIDE PROBE SK3

```
GACGACTACC ACCANACNAT    20
   T    T  T    T
NGANACNATN GC            32
```

SORBITOL KINASE, PROCESS FOR PRODUCING THE SAME, AND SUBSTANTIALLY PURE MICROORGANISM

This application is a 331 of PCT/JP95/01997 filed Sep. 29, 1995 and claims priority under 35 U.S.C. 119 of Japanese application Ser. No. 6/243539 filed Oct. 7, 1994 and 6/247,419 filed Oct. 13, 1994.

FIELD OF THE INVENTION

This invention relates to a sorbitol kinase, which has properties utilizing mainly ATP, but not substantially phosphoenolpyruvate, as the phosphate donor, having N-terminal amino acid sequence (SEQ ID NO: 10) of the formula Met — Arg — Ile — Gly — Ile — Asp — Leu — Gly — Gly — Thr —

— Lys — Thr — Glu — Val — Ile — Ala — Leu — Ser — Glu — Gln with stability up to 60° C. DNA expressing the said sorbitol kinase, a process for producing sorbitol kinase comprising sorbitol kinase producing microorganism belonging to genus Erwinia in a medium and isolating sorbitol kinase therefrom, a substantially pure microorganism which produces said sorbitol kinase and process for producing sorbitol kinase using the said substantially pure microorganism.

PRIOR ARTS

Sorbitol is a representative substance in polyol, and is generated from glucose by aldose reductase.

In diabetes mellitus, when hyperglycemic condition occurred and intracellular hypergeneration of sorbitol continues, sorbitol is accumulated excessively in the cells due to less extracellular difusion of sorbitol, then various failure will occurres caused by accumulation of sorbitol. Accordingly, exact determination of sorbitol is important to find out disease condition of patients with diabetes mellitus.

Sorbitol is known to exist, especially in the crystalline lens, nerves and erythrocytes. Assay of sorbitol has been attempted for various organs. An amount of sorbitol in the erythrocytes converted into whole blood is the levels of approximately 10 $\mu$M–50 $\mu$M even in the patients with diabetes mellitus. (J. Malone et al.: Red cell sorbitol: An indicator of diabetic control. Diabetes: 861–864, 1980) Accordingly, no precise determination could be made.

Assay methods of sorbitol were knwon including, for example, gas chromatography, HPLC and enzymatic method using sorbitol dehydrogenase. Among them, gas chromatography and HPLC methods for determination of sorbitol are quite complicated. Enzymatic method using sorbitol dehydrogenase is quite disadvantage due to low substrate specificity of sorbitol dehydrogenase for sorbitol and sorbitol could not be assayed precisely.

We have searched in the references an enzyme having activity for sorbitol, and found 2 types of enzyme; i.e. sorbitol kinase from silk worm eggs having optimum pH approx. 9.5 and utilizing ATP and phosphoenol pyruvate as a phosphate donor (T. Yaginuma and O. Yamashita, Comp. Biochem. Physiol. 98B(1), 135–141, 1991) and hexokinase, from bovine and human eye lens, having sorbitol activity which utilize ATP as a phosphate donor and utilizing substrates of sorbitol and glucose (S. Srivastava et al. Biochim. Biophys. Acta, 717(2), 210–214, 1982). ATP is utilized mainly as a phosphate donor. Application of sorbitol kinase for practical use by extracting from silk worm eggs and bovine and human eyes is almost impossible. Futhermore, superior heat stability of the enzyme is not disclosed in the prior references.

Sorbitol kinase from microorganisms origin of Aerobacter aerogenes (N. E. Kelker and R. L. Anderson, J. Bacteriol., 160–164, 1971) has known. However, optimum pH of 7.6 and phosphoenolpyruvate as a phosphate donor have only disclosed in the reference, and no description on superior heat stability.

PROBLEMS TO BE SOLVED BY THE INVENTION

Production of sorbitol kinase from the origin except for microorganisms is known to be trace amount which can only be measured by radioisotope, consequently substantial isolation of the enzyme is impossible and no practical use has known. Sorbitol kinase from microorganism origin has property for only utilize phosphoenolpyruvate as a phosphate donor and does not utilize ATP, consequently practical use for diagnostic enzyme is doubtful.

We have extensively made search sorbitol kinase of microorganism origin having superior substrate specificity for sorbitol with utilizing ATP as a phosphate donor, and found sorbitol kinase, which utilize ATP, but not substantially phosphoenolpyruvate, as the phosphate donor and is stable up to 60° C., in a culture of Erwinia sp. SK-472-20 (FERM BP-4492).

Production capacity of sorbitol kinase from Erwinia sp. SK-472-20 is very small, accordingly excellent production method by recombinant DNA technology has been expected to develop.

If mass production of sorbitol kinase can be made by Erwinia sp. SK-472-20, a composition for simple quantitative analysis of sorbitol can be provided by combining with sorbitol-6-phosphate dehydrogenase produced, for example, by Comamonas sp. SY-77-1 FERM BP-4810.

We have tried to isolate sorbitol kinase gene of Erwinia sp. SK-472-20 and searched DNA sequence and amino acid sequence of sorbitol kinase from the other origins, however no reports have been find out. Namely amino acid sequences of sorbitol kinase depending on the producing organisms could not be estimated.

Under these circumstances, because of low productivity of sorbitol kinasefrom Erwinia sp. SK-472-20, which has high reactivity and stability and is effective for assay of sorbitol, development of microorganism, which produces the enzyme effectively, by genetic engineering technology has been highly expected. However, no reports on essential fundamental informations for genetic engineering production of sorbitol kinase consisting of primary structure of polypeptides and DNA sequences coding amino acid sequences of the said enzyme have known. Accordingly, determination of primary structure of polypeptides constructing sorbitol kinase, DNA sequence coding amino acid sequences of the said enzyme and production of the said enzyme by genetic engineering are essential.

The present invention has completed for the purposes to provide for developing microorganism which produce effectively sorbitol kinase useful for assay of sorbitol, mass production method of the said enzyme using the said microorganism and the said microorganism per se.

MEANS FOR SOLVING THE PROBLEMS

We have studied practically useful sorbitol kinase for diagnostic enzyme and process for production thereof, and found that a strain SK-472-20 of genus Erwinia isolated from a soil sample collected from the field in Hiroshima City produced sorbitol kinase. Futher we have found that the isolated sorbitol kinase utilized mainly ATP, but not substantially phosphoenolpyruvate, as a phosphate donor, and completed the present invention.

Further, we have studied to complete the above objects and screened gene DNA expressing sorbitol kinase from chromosomal DNA library of microorganism origin which produced the said enzyme, followed by constructing expression vector using the said DNA. The DNA was inserted into a microorganism, for example, belonging to *Escherichia coli* (hereinafter sometimes designates as *E.coli*) to produce transformant which was cultured in a medium, then we have found that the said sorbitol kinase was effectively produced in large quantity. The present invention has completed by the above findings.

An object of the present invention is to provide sorbitol kinase having the following biochemical properties.

(1) Enzyme action

Enzymatic action on sorbitol as a substrate is as follows. Utilizing mainly ATP but not phosphoenolpyruvate as a phosphate donor.

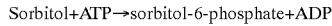

Sorbitol+ATP→sorbitol-6-phosphate+ADP (2) Substrate specificity

Substrate specificity on sorbitol.

(3) N-terminal amino acid sequence

Containing the following sequence:

(SEQ ID NO: 10)

Met—Arg—Ile—Gly—Ile—Asp—Leu—Gly—Gly—

—Thr—Lys—Thr—Glu—Val—Ile—Ala—Leu—Ser—Glu—Gln (4) Heat stability

Stable at least up to 60° C. when a 100 mM Tris-HCl buffer (pH 8.5, containing 0.5 U/ml of sorbitol kinase) is heated for 15 minutes at various temperatures and the residual activity is measured.

Another object of the present invention is to provide a process for production of sorbitol kinase comprising culturing sorbitol kinase producing microorganism belonging to genus Erwinia and isolating the sorbitol kinase from the cultured mass.

Further object of the present invention is to provide a polypeptide substantially coding amino acid sequence SEQ ID NO: 2 consisting of amino acid Nos. 1 to 313 (FIG. 9) shown in SEQ ID NO: 1 which showing novel sorbitol kinase utilizing ATP, but not substantially utilizing phosphoenolpyruvate, as a phosphate donor.

More further object of the present invention is to provide DNA having base sequence substantially coding amino acid sequence consisting of amino acid Nos. 1 to 313 shown in SEQ ID NO: 1.

Still further object of the present invention is to provide a process for production of sorbitol kinase comprising culturing sorbitol kinase producing substantially pure microorganism, which is the microorganism transformed by recombinant plasmid having base sequence substantially coding amino acid sequence consisting of amino acid Nos. 1 to 313 shown in SEQ ID NO: 1, and isolating sorbitol kinase from the cultured mass.

Still more further object of the present invention is to provide a microorganism transformed by recombinant plasmid having base sequence substantially coding amino acid sequence consisting of amino acid Nos. 1 to 313 shown in SEQ ID NO: 1.

The present invention is explained in details in the following.

The sorbitol kinase producing microorganism of the present invention is not limited if it has an ability to produce sorbitol kinase and belongs to genus Erwinia, including variants and mutants which produce sorbitol kinase. Preferable example of the microorganism is a strain SK-472-20 belonging to genus Erwinia.

Taxonomical properties of the strain are as follows.

Identification of the strain was made in accordance with Determinative Medical Bacteriology (2nd Ed.), Microbiological methods (Vol. 3). Results were refered to Determinative Medical Bacteriology (2nd Ed.), Bergey's Manual of Systematic Bacteriology, Vol. 1 and 2, Int. J. Syst. Bacteriology.

Specific Characters on Growth

Bouillon plate medium

Circular shape with round edges. Smooth surface with creamy—grayish white. Lustered. Opaque. No production of soluble pigment.

Buillon liquid medium

Good growth with uniform growth.

Litmus milk medium and BCP milk mediuim

Acidic with coagulation.

Morphological Characters

Bacillus with round edges, 0.59×1.38 μm in size. Peritrichal movement (it could not clearly be observed by flagellar staining and electron microscope, but could be determined by motilities with changing direction and zigzag movement according to observation of bacterial motility in spreading growth in motility test and microscopic observation).

No polymorphism. No sporulation.

| Physiological and biochemical characters | |
|---|---|
| Gram stain | − |
| Acid-fast stain | − |
| OF test (Hugh-Lefuson) | FG |
| OF test (nitrogen source: NH$_4$H$_2$PO$_4$) | FG |
| Aerobic growth | + |
| Anaerobic growth | + |
| Growth temperature: | |
| 51° C. | − |
| 46.2° C. | + |
| 30° C. | + (optimum temp.) |
| 12° C. | + |
| Halotolerance: | |
| 0% | + |
| 5% | + |
| 7% | + |
| 10% | + |
| Growth pH: | |
| 3.43 | − |
| 4.32 | + |
| 7.0 | + (optimum pH) |
| 9.91 | + |
| 10.31 | − |
| Decomposition activity | |
| gelatin | − |
| casein | − |
| esculin | + |
| cellulose | − |
| tyrosine | − |
| arginine | − |

-continued

| Physiological and biochemical characters | |
|---|---|
| starch | (+) |
| Enzyme productivity | |
| catalase | + |
| oxidase | − |
| urease (SSR) | − |
| urease (Chris.) | + |
| L-lysine decarboxylase | − |
| L-ornithine decarboxylase | + |
| DNase | − |
| β-glucuronidase | − |
| Productivity | |
| indol | − |
| H₂S (SIM medium) | + |
| H₂S (TSI medium) | + |
| MR test | − |
| VP test | + |
| Nitrate reduction | + |
| Nitrite reduction | + |
| Utilization in Simmons medium (alkaline formation) | |
| citrate | + |
| malate | + |
| maleinate | − |
| malonate | + |
| propionate | − |
| gluconate | − |
| succinate | + |
| Utilization in Christenssen mediium (alkaline formation) | |
| citrate | + |
| malate | + |
| maleinate | − |
| malonate | + |
| propionate | − |
| gluconate | + |
| succinate | + |
| Acid formation from sugar | |
| adonitol | − |
| L(+) arabinose | + |
| cellobiose | + |
| dulcitol | − |
| meso-erythritol | − |
| D-fructose | + |
| D-galactose | + |
| D-glucose | + |
| glycerin | + |
| inositol | + |
| inulin | − |
| lactose | + |
| maltose | + |
| D-mannitol | + |
| D-mannose | + |
| melezitose | − |
| melibiose | + |
| D-raffinose | + |
| L(+)-rhamnose | + |
| D-ribose | + |
| salicin | + |
| L(−)-sorbose | + |
| sorbitol | + |
| starch | + |
| saccharose | + |
| trehalose | + |
| D-xylose | + |
| Gas formation from sugar | |
| D-glucose | + |
| lactose | + |
| Utilization of inorganic nitrogen sources | |
| nitrate | − |
| ammonium salt | + |
| Deamination of phenylalanine | − |

As shown in the above, major properties of the strain are summarized as follows. Gram negative bacillus with peritrichal motility. Catalase positive, oxidase negative and facultative anaerobe. Fermentative decomposition of glucose with generation of acid and gas.

The strain belongs Enterobacteriaceae because of Gram positive facultative anaerobic bvacteria of oxidase nonproducer. Since many genera are known to belong Enterobacteriaceae, genus Erwinia and genus Enterobacter may be applicable to the strain. However, no genus Enterobacter is known to produce hydrogen sulfate in TSI medium, accordingly the strain is referred to genus Erwinia. In general, although genus Erwinia is non-production of gas and urease, however there may be some exceptions in genus Erwinia. Three exceptional species and the present strain are compared with each other.

Table shows comparison of following strains.

The present strain;
A: *Erwinia chrysanthemi;*
B: *Erwinia cypripedii;*
C: *Erwinia nigrifluens.*

| | The strain | A | B | C |
|---|---|---|---|---|
| Motility | + | + | + | + |
| Anaerobic growth | + | + | + | + |
| H₂S production from cystein | + | + | + | + |
| Acetoin production | + | + | − | + |
| Urease production | + | − | − | + |
| Production of gas from glucose | + | + | + | − |
| Casein hydrolysis | − | d | − | − |
| Gelatin hydrolysis | − | + | − | − |
| Deamination of phenylalanine | − | − | + | − |
| Indol production | − | + | − | − |
| Nitrate reduction | + | + | + | − |
| Growth in 5% NaCl | + | d | + | ND |
| DNase production | − | − | − | − |
| Decomposition of esculin | + | + | + | + |
| Acid production from sugar | | | | |
| saccharose | + | − | − | − |
| melibiose | + | + | + | + |
| inositol | + | d | + | + |
| raffinose | + | + | − | + |
| malitose | + | − | + | − |
| L(+) arabinose | + | + | + | + |
| sorbitol | + | + | + | + |
| ribose | + | + | + | + |
| mannose | + | + | + | + |
| mannitol | + | + | + | + |
| cellobiose | + | + | + | − |
| lactose | + | d | − | − |
| rhamnose | + | + | + | + |
| salicin | + | + | + | + |
| xylose | + | + | + | + |
| trehalose | + | − | + | + |
| dulcitol | − | − | − | − |
| glycerin | + | + | d | + |
| adonitol | − | − | − | − |
| melezitose | − | − | − | − |
| starch | + | − | − | − |

+: positive, −: negative, d: different in strains, ND: no data.

As shown in the above, the present strain has no similar strain in comparison with the other strains. Accordingly, the present strain was referred as Erwinia sp. SK-472-20, and has been deposited in National Institute of Bioscience and Human-Technology, 1–3, Higashi 1 chome Tsukuba-shi Ibaraki-ken, 305 Japan on Dec. 10, 1993 as FERM BP-4492.

We have found that the strain genus Erwinia produced sorbitol kinase and examined purification and properties of the enzyme.

The strain used in the present invention is a sorbitol kinase producing strain such as Erwinia sp. SK-472-20.

In the present invention, liquid culture and solid culture can be applicable, however aeration culture may be preferable for industrial production. Cultivation media used for production can include common carbon sources, nitrogen sources, inorganic salts and other nutrient sources used in culture of microorganisms. Other assimilable nutrient sources for microorganisms genus Erwinia can be used.

Examples of carbon sources are glucose, fructose, saccharose, xylose, maltose, glycerol, dextrin, starch, amino acids, fatty acids, oil and organic acids, in combination or alone. Examples of nitrogen sources are inorganic or organic nitrogen. Examples of inorganic nutrients are ammonium sulfate, ammonium nitrate, urea, sodium nitrate and ammoniuim chloride. Examples of organic nitrogen sources are powder of soybean, rice, corn and wheat, corn steep liquor, peptone, meat extract, casein, amino acids and yeast extract. Examples of inorganic salt and trace nutrients are salt of phosphate, magnesium, potassium, iron, calcium or zinc. Other components, which can be used for bacterial growth and stimulate production of sorbitol kinase, such as vitamins, non-ionic surface active agents and untifoam agents can be used, if necessary.

Cultivation can be proceeded by aerobic conditions within cultivation temperature for growth of the bacteria and production of sorbitol kinase, generally at 15°–37° C., preferably at 25° C.–35° C. Culturing time depends on the condition and can be continued until the maximum production of sorbitol kinase, generally for 24–100 hours.

The thus produced sorbitol kinase accumulated generally in the cells, consequently it can be extracted from bacterial cells. Extraction of sorbitol kinase can be performed by separating the cells from cultured mass, suspending the obtained wet cells in phosphate buffer or Tris-HCl buffer solution and subjected to combination of treatments for microbial cells such as lysozyme treatment, ultrasonication, French-press and dynamil to obtain the crude sorbitol kinase solution.

Sorbitol kinase can be isolated by treatments of known isolation and purification methods for proteins and enzymes from the crude sorbitol kinase solution. For example, the crude sorbitol kinase solution was subjected to fractional precipitation using organic solvent such as acetone, methanol and ethanol, or salting out using ammonium sulfate or sodium chloride to precipitate and isolate sorbitol kinase. The precipitate is treated, if necessary, by dialysis and isoelectric precipitation, and is purified by electrophoresis and column chromatography using ion-exchanger, gel-filtration agents and adsorbents. If necessary, combination of these treatments can be applied for obtaining purified sorbitol kinase.

The thus obtained enzyme can be treated by ultrafiltration and lyophilization with or without adding salts, sugars, proteins, lipids and surface active agents to obtain liquid or solid sorbitol kinase. In the lyophilization, saccharose, mannitol, sodium chloride or albumin can be added in its amount of 0.5–10% as a stabilizer.

Physicochemical properties and assay method of sorbitol kinase are explained as follows.

Assay Method of Sorbitol Kinase

One milliliter of a reaction mixture consisting of 0.2M Tris-HCl buffer solution (pH 8.5) 0.2 ml, 0.1M ATP 0.02 ml, 0.1M $MgCl_2$ 0.02 ml, 100 U/ml sorbitol-6-phosphate dehydrogenase (refer to referential example) 0.05 ml, 10 mM NAD 0.1 ml, 100 U/ml diaphorase (Asahi Chemical Ind. Co.) 0.05 ml, 0.25% NTB 0.1 ml, 1M sorbitol 0.1 ml, 10% Triton X-100 0.01 ml and distilled water 0.3 ml was pre-heated at 37° C. for 1 minute, and the enzyme solution 20 μl was added thereto, then the mixture was incubated for 10 minutes.

Reaction was terminated by adding 0.1N HCl 2 ml and optical density of the mixture was measured using 1.0 cm cell at 550 nm within 5 minutes (As). Also optical density of distilled water 20 μl in place of the enzyme solution was measured in the same manner as above as a blank test (Ab). Enzymatic activity is determined by difference in the absorption between the optical density of the enzyme solution (As) and the blank test (Ab), i.e. (As–Ab). A unit of enzyme activity is defined as an amount of enzyme which generate 1 μm of reduced NAD in one minutes at 37° C. and calculated by the following equation.

Enzyme activity (U/ml)=(As–AB)×0.795×dilution rate of enzyme

Physicochemical Properties (1) Enzyme action

Enzyme action using sorbitol as a substrate is illustrated as follows.

Sorbitol+ATP sorbitol-6-phosphate+ADP (2) Substrate specificity

Substrate specificity for sorbitol is indicated. Substrate specificities on various substrates are shown in Table 1.

TABLE 1

| Substrate | Relative activity (%) |
| --- | --- |
| Sorbitol | 100 |
| Glycerol | 0 |
| Xylose | 0 |
| Inositol | 0 |
| Saccharose | 0 |
| Mannitol | 0 |
| Maltose | 0 |
| Treharose | 0 |
| Glucose | 0 |
| Mannose | 0 |
| Galactose | 0 |
| Fructose | 0 |
| Lactose | 0 |
| N-acetylglucosamine | 0 |
| 2-deoxyglucose | 0 |
| Fructose-1-phosphate | 0 |
| Glucose-6-phosphate | 0 |
| Galactose-1-phosphate | 0 |

(3) Phosphate donor

Relateive activities for GTP, ITP and UTP, when activity for ATP (final concentration 2 mM) is set as 100%, are 11.8%, 40.5% and 3.6%, respectively, accordingly phosphate donor or the enzyme is ATP. No substantial utilization of phosphoenolpyruvate is observed when phosphoenolpyruvate is replaced by ATP for assaying enzyme activity.

(4) Isoelectric point 4.8±0.5 (electrophoresis using carrier ampholytes)

(5) Molecular weight

50000±5000 (gel-filtration using TSK-G3000SW$_{XL}$)

35000±5000 (SDS polyacrylamide electrophoresis)

(6) Optimum pH

Optimum pH is measured by the above enzyme assay method. Results are shown in FIG. 1. In FIG. 1, 100 mM phosphate buffer is used for pH 6.0–8.0 (-○-); 100 mM Tris-HCl buffer for pH 7.0–9.0 (-●-); and 100 mM glycine-sodium hydroxide buffer for pH 9.0–10.5 (-□-). Optimum pH is 8.5–9.5.

(7) pH stability 100 mM buffer solutions containing sorbitol kinase 0.5 U/ml were treated at 60° C. for 15 minutes, and remaining activity was measured by the above enzyme assay method. Results are shown in FIG. 2. In FIG. 2, 100 mM acetate buffer is used for pH 4.5–6.0 (-○-); 100 mM phosphate buffer for pH 6.0–8.0 (-●-); 100 mM Tris-HCl buffer for pH 7.0–8.5 (-□-); and 100 mM glycine-sodium hydroxide buffer for pH 9.0–10.5 (-■-). Most preferable stability is observed at pH 6.5–10.0.

(8) Optimum temperature

Optimum temperature of the enzyme was measured by changing temperature range at 37° C.–60° C. according to the above assay method. Result is shown in FIG. 3, in which optimum temperature of the present enzyme is approx. 50° C.

(9) Heat stability 100 mM Tris-HCl buffer solution (pH 8.5) containing sorbitol kinase 0.5 U/ml was treated at various temperatures for 15 minutes, and remaining activity was measured by the above enzyme assay method. Results are shown in FIG. 4 in which the enzyme is stable at least up to 60° C.

(10) Effects of metal ions and chemical modifiers on enzyme activity

Effect of various metal ions (2 mM) on the enzyme in the presence of 2 mM magnesium ion is shown in Table 2.

TABLE 2

| Metal ion and chemical modifier | Relative activity (%) |
| --- | --- |
| None | 100 |
| LiCl | 74.3 |
| NaCl | 112 |
| KCl | 180 |
| CsCl | 85 |
| $CuCl_2$ | 0 |
| $NiCl_2$ | 14.5 |
| $CoCl_2$ | 17.3 |
| $CaCl_2$ | 44.6 |
| EDTA | 0 |
| $NaN_3$ | 123 |

As shown in the Table 2, the enzyme of the present invention was inhibited by $CuCl_2$, $NiCl_2$, $CoCl_2$ and EDTA, and was activated by KCl.

(11) N-terminal amino acid sequence

N-terminal amino acid sequence of the enzyme is as follows.

(SEQ ID NO: 10)
Met—Arg—Ile—Gly—Ile—Asp—Leu—Gly—Gly—

—Thr—Lys—Thr—Glu—Val—Ile—Ala—Leu—Ser—Glu—Gln

As explained in the above, sorbitol kinase of the present invention utilizes mainly ATP, but not phosphoenolpyruvate, as a phosphate donor and is stable at least up to 60° C., consequently it is different from sorbitol kinase of *Aerobacter aerogenes*. Further the enzyme activated by KCl, consequently it is different from known sorbitol kinase.

Genetic manipulation in relation to the enzyme of the present invention is explained in details.

In the present invention, sorbitol kinase expressing gene DNA used for preparing transformed microorganism which produces sorbitol kinase can be obtained, for example, by screening from chromosomal DNA library originated from the said enzyme producing microorganism.

Erwinia sp. SK-472-20 is preferably used for production of sorbitol kinase of the present invention. Methods for screening the enzyme expressing gene DNA from chromosomal DNA library of Erwinia sp. SK-472-20 is exemplified. At first, chromosomal DNA of the said microorganism at about 100–2000 µg is extracted by conventional method.

Plasmid, to which sorbitol kinase coding gene DNA is inserted, is constructed. Vector for preparation of library is preferably constructed for genetic recombinant from autonomously growing phage or plasmid in the host cells. Examples of the above phage are λgt·λC and λgt·λB for host microorganims *E.coli*. Examples of plasmids for host microorganims *E.coli* are pBR322, pBR325, pACYC184, pUC12, pUC13, pUC18, pUC19, pUC118, pUC119, bluescript SK+, bluescript KS+, bluescript SK−, bluescript KS−, bluescript SKII+, bluescript KSII+, bluescript SKII− and bluescript KSII−. Examples of plasmids for host microorganims genus Bacillus and genus Saccharomyces are pHY300PLK and pYAC5, respectively.

Insertion method of sorbitol kinase gene into the vector is not limited, and conventional methods can be used. For example, the extracted chromosomal DNA 1–10 µg of the said microorganism is treated by preferable restriction enzyme, as well as being treated the vector 1–10 µg for preparation of library by preferable restriction enzyme. After annealing each cohesive end, the sequence is ligated by using preferable DNA ligase and transformed in the host microorganism to prepare chromosomal DNA library.

Examples of preferable host microorganism are *E.coli*. Insertion of the constructed plasmid into *E.coli* is preferably made by competent cell method or calcium phosphate method. Selection of gene transfer into the host microorganism can be made by culturing the said host microorganism in selective medium based on drug resistance marker of vector consisting of recombinant DNA to select growing host microorganism.

Meanwhile, N-terminal amino acid sequence of the authentic sorbitol kinase, i.e. amino acid sequence of lysyl endopeptidase treated fragments, is determined. Various oligonucleotides were synthesized based on the above sequence and isotope labelled oligonucleotides were prepared.

Recombinant *E.coli* having sorbitol kinase expressing gene is expected to be screened from the above chromosomal DNA library by the conventional method using the radio active oligonucleotide prove. However, the process of this screening is very difficult in the present invention, and the clones bearing sorbitol kinase gene could not be found out in spite of preparing various probes from partial amino acid sequence of sorbitol kinase.

In design of probe, the probe is synthesized by selecting generally estimated sequence of DNA sequence combination as little as possible. In sorbitol kinase of the present invention, sequence with less combination does not exist. Consequently, we have prepared the probes by narrowing the combination down from various combination with referring to use frequency of codon of Erwinia gene. Further, probes consisting of inosine in the multiple estimated parts were prepared. Length of the probes is also examined. Furthermore, hybridization and washing conditions (composition of solution, temperature and time) are examined. Finally, in the present invention, as explained in the examples hereinbelow, recombinant *E.coli*, which was selected by using radioactive oligonucleotide probes based on N-terminal amino acid sequence, being hybridized with specific condition and washing, is found to bear the desired gene DNA.

A recombinant plasmid (designated as pSK1) containing DNA with sorbitol kinase gene can be prepared from the recombinant library containing the said gene DNA according to a method of Maniatis et al. [Molecular Cloning: Cold Spring Harbor (1982)]. Schematic diagram of construction of the said plasmid is shown in FIG. 12. Restriction map of a part originated from chromosomal DNA of Erwinia sp. SK-472-20 in the said plasmid is shown in FIG. 11.

Base sequence of the part originated from chromosome in the plasmid in FIG. 12 was determined by dideoxy method ["Science" 214: 1205–1210, 1981], and was confirmed to contain whole DNA coding sorbitol kinase, as well as determining the total base sequence. It contains at least a sequence shown in FIG. 10. Complete identification with the expression of sorbitol kinase of the present invention, N-terminal amino acid sequence of sorbitol kinase and the identical frame of amino acid sequence in lysylendopeptidase treated fragment could show that sorbitol kinase of the present invention contains amino acid seqeuence in FIG. 9.

In the sequences of FIG. 9 and FIG. 10, substantially similar sequence relating to sorbitol kinase activity is included in the present invention.

Expression of sorbitol kinase can preferably be made using pSK1. Alternatively, expression vector, to which sorbate kinase coding gene DNA is newly inserted, can be constructed. Preferable expression vector is a phage or plasmid constructed for genetic recombinant from autonomously growing phage or plasmid in the host microorganism. Examples of the former phage are, for example, λgt·λC and λgt·λB for *E.coli*. Examples of plasmid are, for example, pBR322, pBR325, pACYC184, pUC12, pUC13, pUC18, pUC19, pUC118, pUC119, bluescript SK+, bluescript KS+, bluescript SK−, bluescript KS−, bluescript SKII+, bluescript KSII+, bluescript SKII- and bluescript KSII-. Examples of plasmids for host microorganims genus Bacillus and genus Saccharomyces are pHY300PLK and pYAC5, respectively.

Insertion method of sorbitol kinase gene into the vector is not limited, and conventional methods can be used. For example, recombinant plasmid DNA and the expression vector containing sorbitol kinase gene DNA are treated using preferable restriction enzyme to obtain DNA fragments and vector fragments containing sorbitol kinase gene. After annealing each cohesive end, each fragment is ligated by using suitable DNA ligase to obtain new expression vector.

Trunsduction of the thus constructed plasmid into *E.coli* and selection of transformation of desired recombinant DNA in the host microorganism can be performed by the methods described hereinbefore.

In the present invention, a transformed microorganism belonging to *E.coli* by the above plasmid pSK1 is designated as *E.coli* DH1-pSK and deposited in National Institute of Bioscience and Human-Technology, 1–3, Higashi 1 chome Tsukuba-shi Ibaraki-ken, 305 Japan, as FERM BP-4496 on Dec. 10, 1983.

Cultivation of the thus prepared transformant microorganism can be performed in a mediuim containing nutrient sources such as carbon sources and nitrogen sources and inorganic substances necessary for microbial growth. Examples of carbon sources are, for example glucose, starch, sucrose, molasses and dextrin. Examples of nitrogen sources are, for example peptone, meat extract, casein hydrolysate, corn steep liquor, nitrate and ammonium salts. Examples of inorganic substances are, for example salt containing cation such as sodium, potassium, calcium, magnesium, cobalt, zinc, manganese and iron, and anion such as chlorine, sulfate and phosphate.

Culturing condition is not limited and is made by conventional process, for example aeration stirring culture, shaking culture, rotary culture and standing culture, generally at 20°–50° C., preferably at 25°–42° C. and more preferably at 37° C. for 12–48 hours.

After cultivation, cultured microbial cells were collected by centrifugation followed by destruction of the cells by enzymatic treatment, autolysis, French press and ultrasonication to prepare extracted enzyme solution. Isolation and purification of the enzyme from the extract can be made, for example, by salting out, desalting and adsorption and desorption using ion-exchange resin. Enzyme is further purified by adsorption chromatography, gel-filtration and electrophoresis.

Enzymatic activity and physico-chemical properties of sorbitol kinase were examined in the purified enzyme, and it was confirmed that the said transformant microorganism has productivity of sorbitol kinase.

Therefore, the gene DNA, which expresses sorbitol kinase used in the present invention, has a nucleotide sequence coding amino acid sequence in FIG. 9, and its nucleotide sequence is a sequence shown in FIG. 10.

The thus obtained sorbitol kinase has similar catalytic action and enzymatic properties as same as the sorbitol kinase of the strain Erwinia sp. SK-472-20 (FERM BP-4492). Namely, the enzyme catalyses a reaction generating D-sorbitol-6-phosphate and ADP from D-sorbitol and ATP. The enzyme utilizes ATP, but substantially not phosphoenolpyruvate, as a phosphate donor. In the substrate specificity, when relative activity on sorbitol is set at 100%, then the relataive activities on fructose, glucose, galactose, mannose, inositol, saccharose, maltose and lactose are 0%. Molecular weight measured by SDS acrylamide gel-chromatography is 35,000±4,000. Isoelectric point is 4.80±0.5.

Optimum pH is 8.5–9.5. Stable up to 60° C. and pH stability is pH 6.5–10.0. The enzyme is inhibited by metal ions of copper, nickel and cobalt, and EDTA, and activated by calcium ion.

The thus obtained sorbitol kinase is useful for diagnostic enzyme for determination of serum sorbitol.

Symbols of nucleotide sequence and amino acid sequence in the specification are based on trivial abbreviation and are listed as follows. All amino acids are L-form.

DNA: deoxyribonucleic acid
A: adenine
T: thmine
G: guanine
C: cytosine
H: adenine, thymine or cytosine
N: adenine, thymine, guanine, cytosine or other base
R: adenine or guanine
Y: thyamine or cytosine
Ala: alanine
Arg: arginine
Asn: asparagine
Asp: aspartic acid
Cys: cysteine
Gln: glutamine
Glu: glutamic acid
His: histidine
Ile: isoleucine
Leu: leucine
Lys: lysine
Met: methionine
Phe: phenylalanine
Pro: proline
Ser: serine
Thr: threonine Trp: tryptophane
Tyr: tyrosine
Val: valine
Xaa: unknown or other amino acid

BRIEF EXPLANATION OF THE DRAWINGS

FIG. 1: Optimum pH curve of sorbitol kinase of the present invention.

FIG. 9: Amino acid sequence (SEQ ID NO: 2) of sorbitol kinase.

FIG. 10: Nucleotide sequence (SEQ ID NO: 1) of sorbitol kinase gene DNA coding amino acids of FIG. 9.

FIG. 13: Amino acid sequence (SEQ ID NO: 3) of N-terminal site of purified authentic sorbitol kinase. Underlined part corresponds to the prepared oligonucleotide probe.

FIG. 14: Amino acid sequence (SEQ ID NO: 4) of lysylendopeptidase site of sorbitol kinase.

FIG. 15: Amino acid sequence (SEQ ID NO: 5) of lysylendopeptidase site of sorbitol kinase. Xaa shows unknown amino acid.

FIG. 16: Amino acid sequence (SEQ ID NO: 6) of lysylendopeptidase site of sorbitol kinase.

FIG. 17: Nucleotide sequence of oligonucleotides used for preparation of oligonucleotide probe.

① Nucleotide sequence (SEQ ID NO: 7) of oligonucleotide probe SK1.

② Nucleotide sequence (SEQ ID NO: 8) of oligonucleotide probe SK2.

③ Nucleotide sequence (SEQ ID NO: 9) of oligonucleotide probe SK3. N shows inosine.

Figure 18:
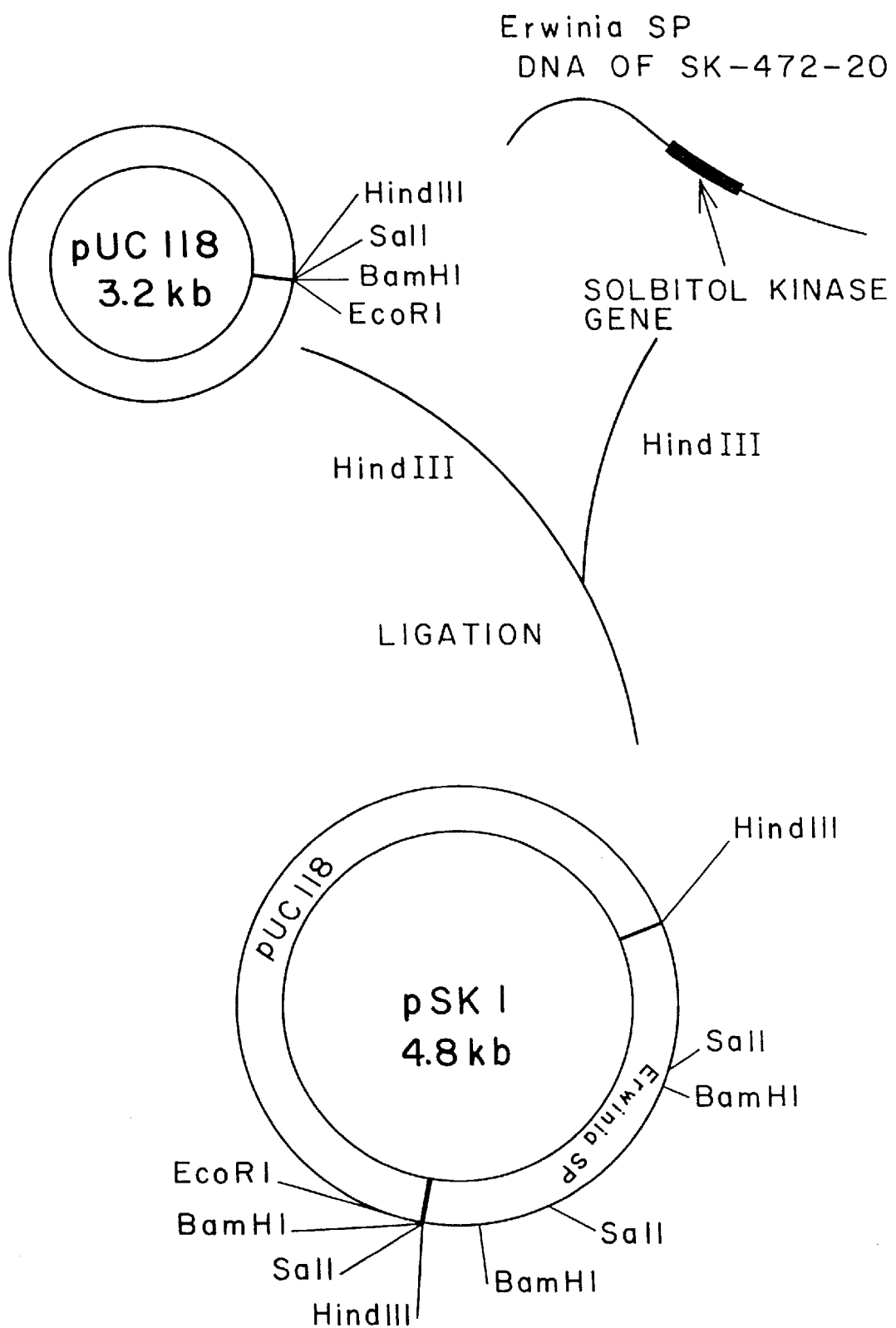

FIG. 18: Schematic drawings of construction of expression vector of sorbitol kinase gene.

EXAMPLES

Following examples illustrate details of the present invention, but are not construed as limiting.

Example 1

Erwinia sp. SK-472-20 was inoculated in five 500 ml flasks, each containing 100 ml of medium (pH 7.0) comprising yeast extract 0.5%, peptone 0.5%, starch 0.1%, $K_2PO_4$ 0.05%, $KH_2PO_4$ 0.05%, $NH_4Cl$ 0.05% and $MgSO_4$ 0.03%, cultured at 28° C. for 48 hours. The obtained seed culture liquid was added in the same medium hereinabove (200 l, pH 7.0) containing antifoam agent and cultured at 28° C. for 25 hours. Cultured mass was centrifuged at 4500 rpm for 30 minutes and microbial cells 560 g was collected.

0.1% lysozyme solution 2 lit. containing 10 mM EDTA and 50 mM Tris-HCl buffer solution (pH 7.5) was added to the microbial cells and incubated at 37° C. for 30 minutes to solublize the cells. Insoluble materials were removed by centrifugation at 4500 rpm for 30 minutes to obtain supernatant solution 1870 ml (41100 U). 5% protamine sulfate 18.7 ml was added to the supernatant solution to remove the precipitate by centrifugation. The thus obtained supernatant solution was dialyzed overnight against 20 mM Tris-HCl buffer solution (pH 8.5), and subjected to ion exchange chromatography of DEAE-Sepharose (2.7×30 cm, Pharmacia Inc.).

Elution was conducted by linear gradient elution with potassium chloride 0–1M and collected the fractions eluted with 0.2–0.3M KCl (31700 U). NaCl was dissolved at concentration of 4M in the enzyme solution, then the solution was subjected to hydrophobic chromatography using phenylSepharose (2.6×19.5 cm, Pharmacia Inc.). Elution was performed by 4M–0M NaCl linear gradient elution to collect the fractions of 1M–0.5M NaCl (20800 U).

The collected enzyme solution was dialyzed overnight against 10 mM Tris-HCl buffer solution (pH 8.5), and subjected to Q-Sepharose ion exchange chromatography (2.6×19.5 cm, Pharmacia Inc.). Elution was performed by 0–0.4M NaCl linear gradient elution to collect the fractions of 0.2–0.25M NaCl (20000 U). The thus obtained enzyme solution was dialyzed overnight against 10 mM Tris-HCl buffer solution (pH 7.5), and subjected to chromatography of hydroxyapatite (1.6×26.5 cm, Pentax Inc.). Elution was performed by 0–0.3M phosphate buffer linear gradient elution to collect the fractions of 0.06–0.1M phosphate buffer (16000 U). The solution was lyophilized to obtain purified sorbitol kinase (213 U/mg, 75 mg).

Referential Example 1

Process for production of sorbitol-6-phosphatae dehydrogenase, which is used for assay of sorbitol kinase of the present invention, by Comamonas sp. SY-77-1, txonomical properties of which were described in U.S. Pat. No. 3,960,662, physico-chemical properties and assay method for enzyme activity are explained hereinbelow. The strain was deposited in National institute of Bioscience and Human-Technology, 1–3, Higashi 1 chome Tsukuba-shi Ibaraki-ken, 305 on Sep. 2, 1994 as FERMBP-4810.

Assay Method of Sorbitol-6-Phosphate Dehydrogenase.

Reaction mixture 1 ml consisting of 0.2M Tris-HCl buffer solution (pH 8.0) 0.25 ml, 0.1M sorbitol-6-phosphate 0.2 ml, 10 mM NAD 0.1 ml, 100 U/ml diaphorase (Asahi Chemical Industry Co.) 0.05 ml, 0.25% NTB (nitrotetrazolium blue) 0.1 ml, 10% Triton X-100 0.01 ml and distilled water 0.29 ml was pre-heated at 37° C. for 1 minute. 0.02 ml of enzyme solution was added thereto and incubated for 10 minutes.

0.1N HCl 2 ml was added to stop the reaction, and within 5 minutes optical absorption of the reaction mixture was measured using pass length 1.0 cm cell at 550 nm (As). Optical density of the blank solution of distilled water 0.02 ml in place of the enzyme solution was measured by the same procedure (Ab). Enzyme activity was measured by the difference (As–Ab) between the optical density of the enzyme solution (As) and that of the blank (Ab). A unit of enzyme is defined as an enzyme amount which produces 1μ mole of reduced NAD at 37° C. for 1 minute. Equation is as follows.

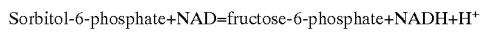

Enzyme activity (U/ml)=(As−Ab)×0.795×enzyme dilution rate

Physico-Chemical Properties (1) Enzyme action

Enzyme action using substrate sorbitol-6-phosphate is shwon as follows.

Sorbitol-6-phosphate+NAD=fructose-6-phosphate+NADH+H⁺

(2) Substrate specificity

Enzyme shows substrate specificity for sorbitol-6-phosphate. Specific activities on various substrates are shown in Table 3.

TABLE 3

| Substrate | Relative activity (5) |
| --- | --- |
| sorbitol-6-phosphate | 100 |
| glucose-1-phosphate | 0 |
| glucose-6-phosphate | 0 |
| galactose-1-phosphate | 0 |
| galactose-6-phosphate | 0 |
| fructose-1,6-diphosphate | 0 |
| glucose | 0 |
| fructose | 0 |
| galactose | 0 |
| mannitol | 0 |
| lactose | 0 |
| mannose | 0 |
| saccharose | 0 |
| treharose | 0 |

(3) Km

Km for sorbitol-6-phosphate 2.0±0.5 (mM), for NAD 0.13±0.05 mM and for thio NAD 0.14±0.05 mM.

(4) Isoelectric point

Isoelectric point of the enzyme measured by electrophoresis using carrier ampholite, pH 3.5–10.0, is 4.8±0.2.

(5) Molecular weight

Molecular weight of the enzyme measured by gel-filtration using TSK-G3000SW (0.75×60 cm. Toso Corp.) is 70,000±5,000.

(6) Optimum pH

Figure 2:
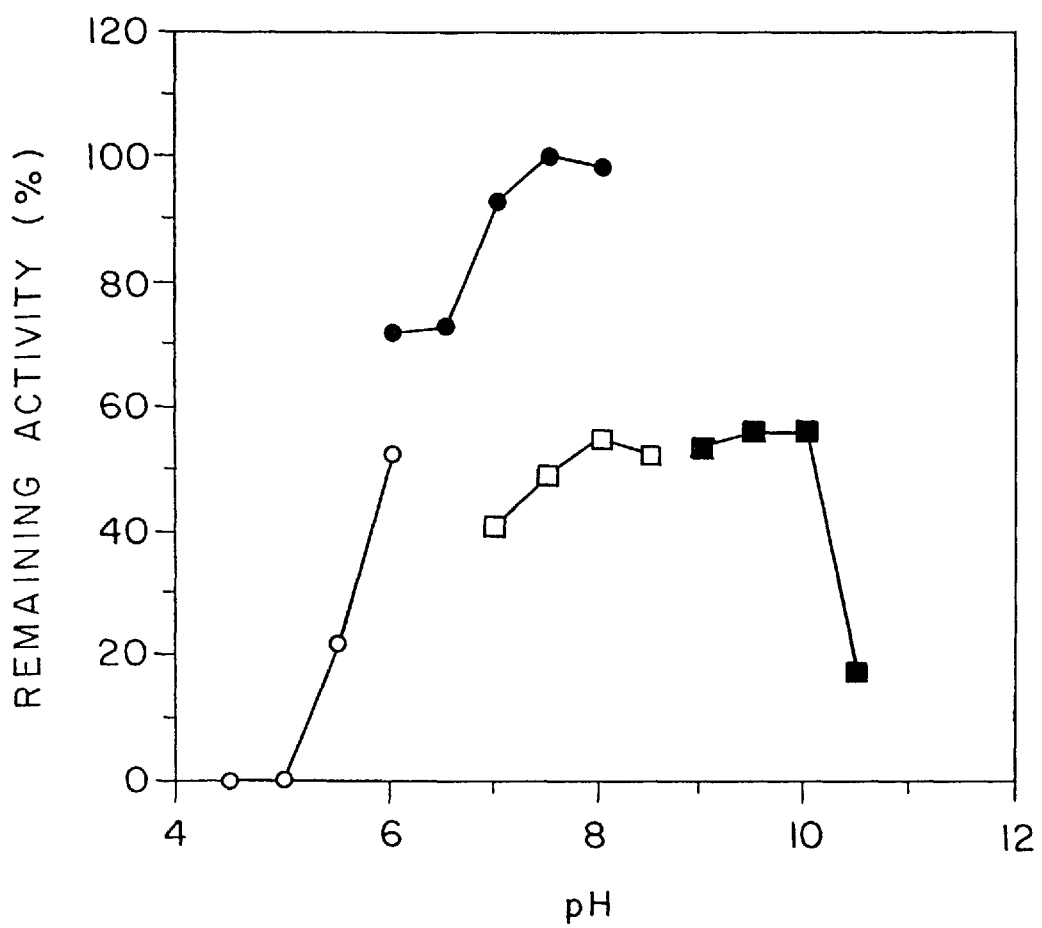
FIG. 2: pH stability curve of sorbitol kinase of the present invention.
Figure 3:
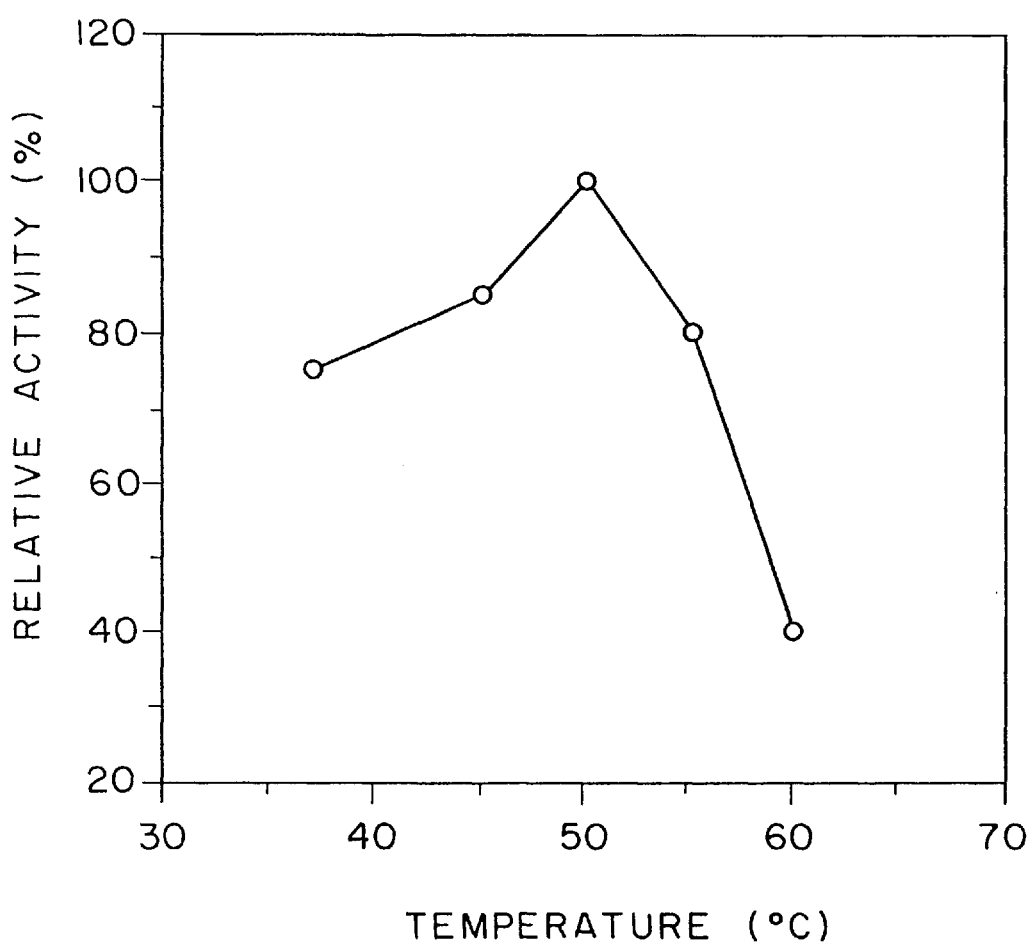
FIG. 3: Optimum temperature curve of sorbitol kinase of the present invention.
Figure 4:
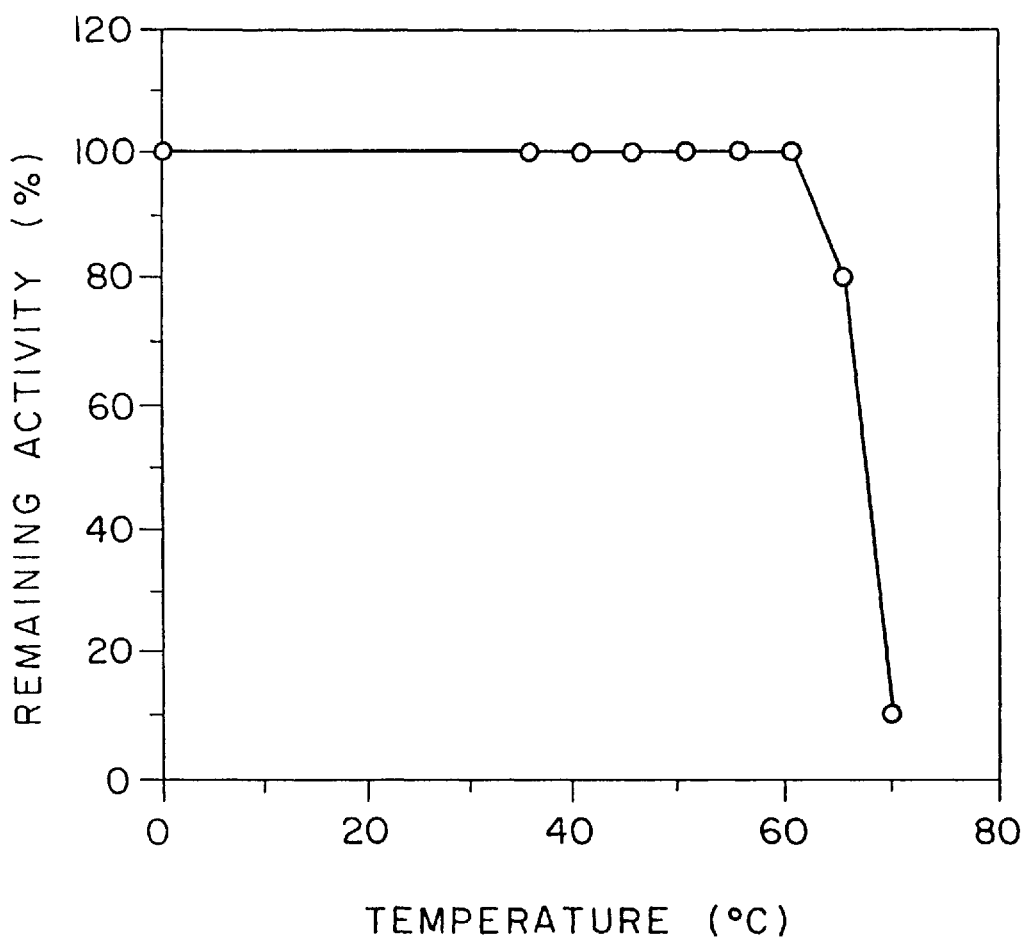
FIG. 4: Heat stability curve of sorbitol kinase of the present invention.
Figure 5:
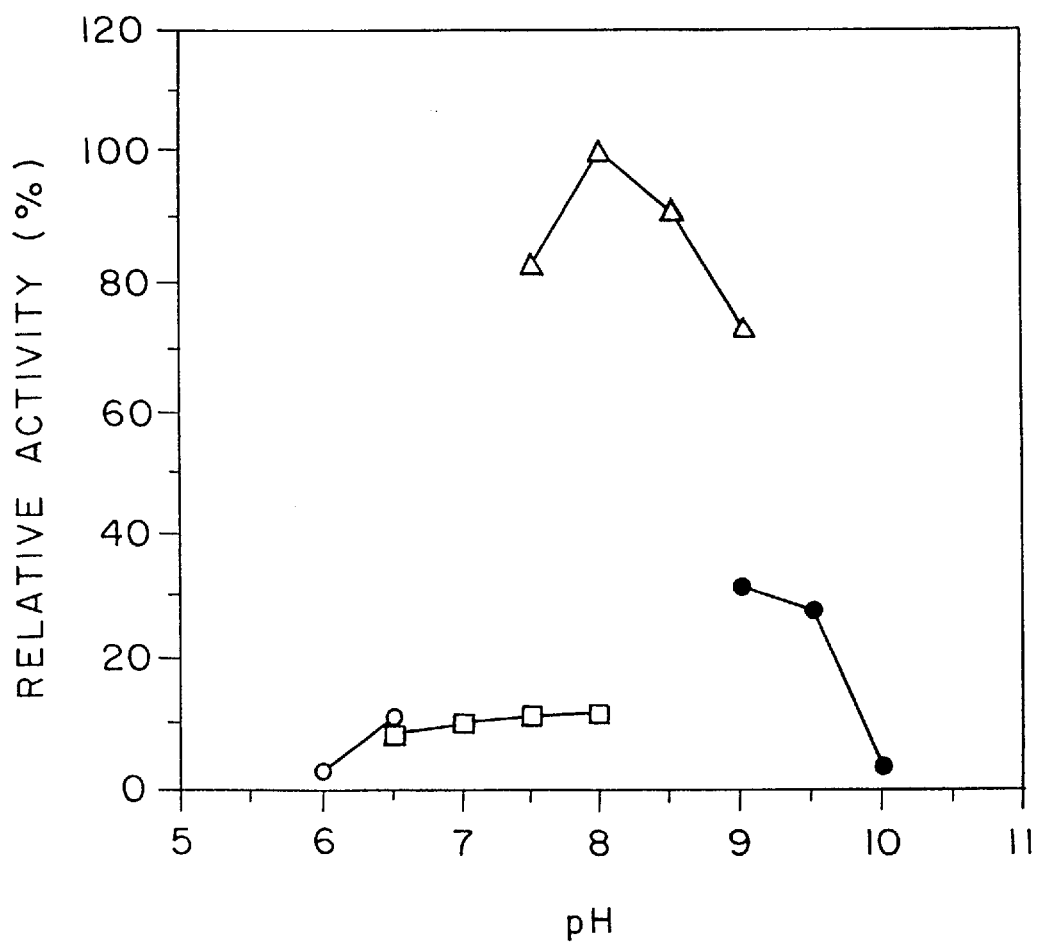
FIG. 5: Optimum pH curve of sorbitol-6-phosphate dehydrogenase.

Optimum pH of the ezmzyme was mesured according to the assay method hereinbefore. Results are shown in FIG. 5. In FIG. 5, activity at pH 6.0–6.5 was measured in 100 mM acetate buffer solution (-○-); 100 mM phosphate buffer solution for pH 6.5–8.0 (-□-); 100 mM Tris-HCl buffer solution for pH 7.5–9.0 (-△-) and 100 mM glycine-sodium hydroxide for pH 9.0–10.0 (-●-). Optimum pH is 8–8.5.

(7) pH stability

Figure 6:
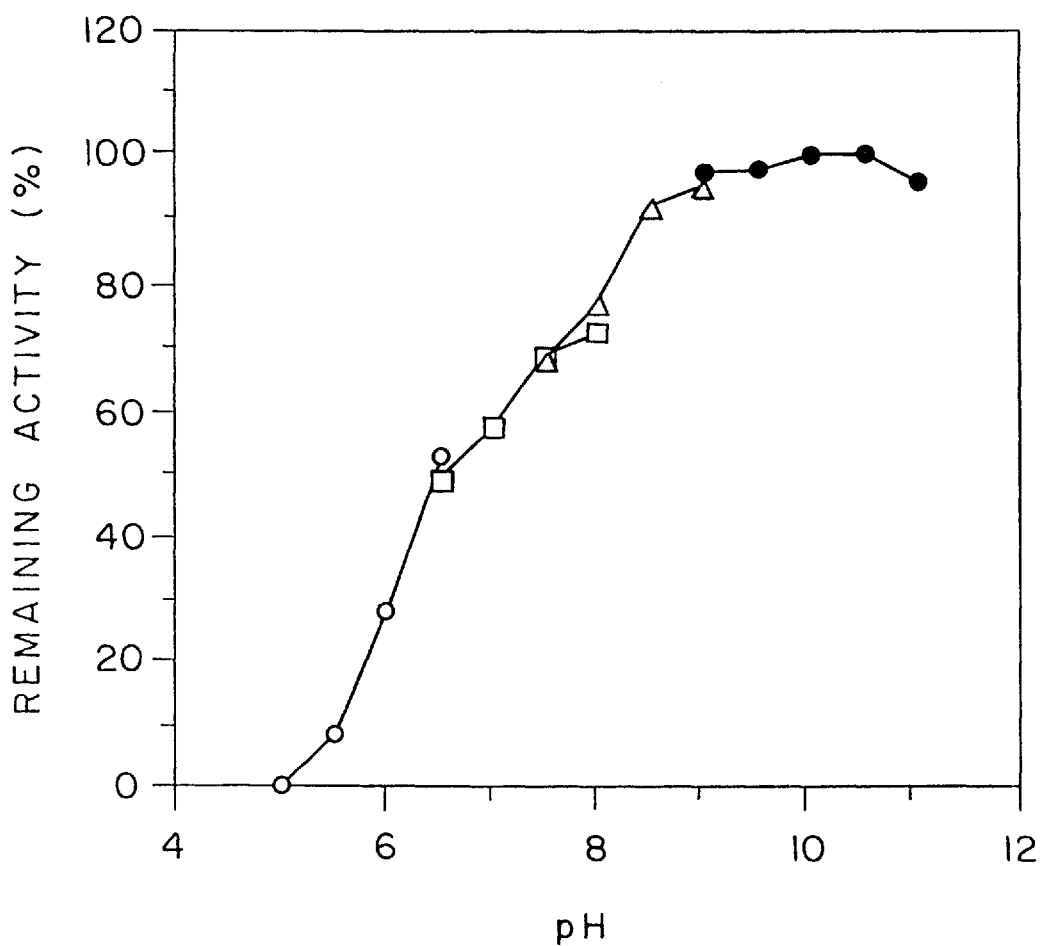
FIG. 6: pH stability curve of sorbitol-6-phosphate dehydrogenase.

Sorbitol-6-phosphate dehydorgenase 1 U/ml was treated in various buffer solution at 37° C. for 60 minutes and remaining activity was measured according to the assay method hereinbefore. Results are shown in FIG. 6. In FIG. 6; 100 mM acetate buffer for pH 5.0–6.5 (-○-); 100 mM phosphate buffer solution for pH 6.5–8.0 (-□-); 100 mM Tris-HCl buffer solution for pH 7.5–9.0 (-△-) and 100 mM glycine-sodium hydroxide for pH 9.0–11.0 (-●-). Most preferred stability is observed at pH 8–11.

(8) Optimum temperature

Figure 7:
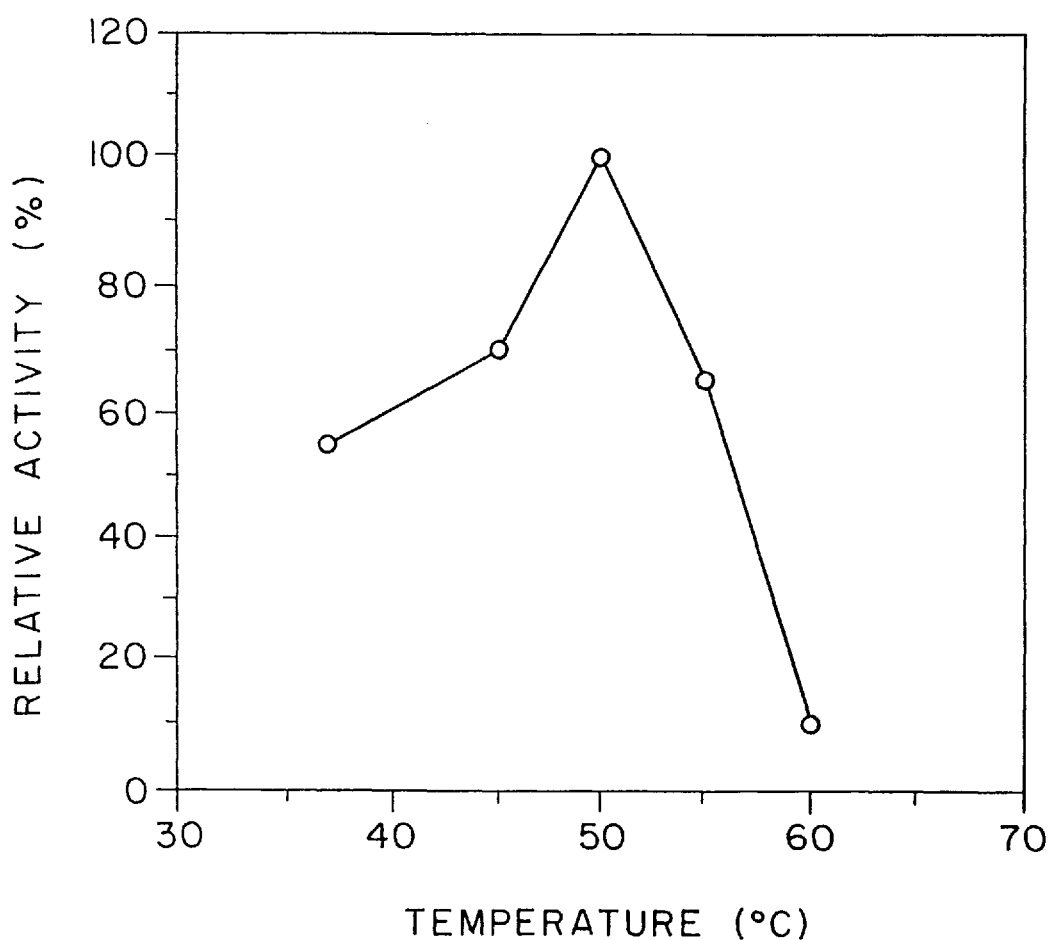
FIG. 7: Optimum temperature curve of sorbitol-6-phosphate dehydrogenase.

Enzyme activity was measured according to the assay method hereinbefore at 37° C.–60° C. Result is shown in FIG. 7. Optimum temperature is approximately at 50° C.

Figure 8:
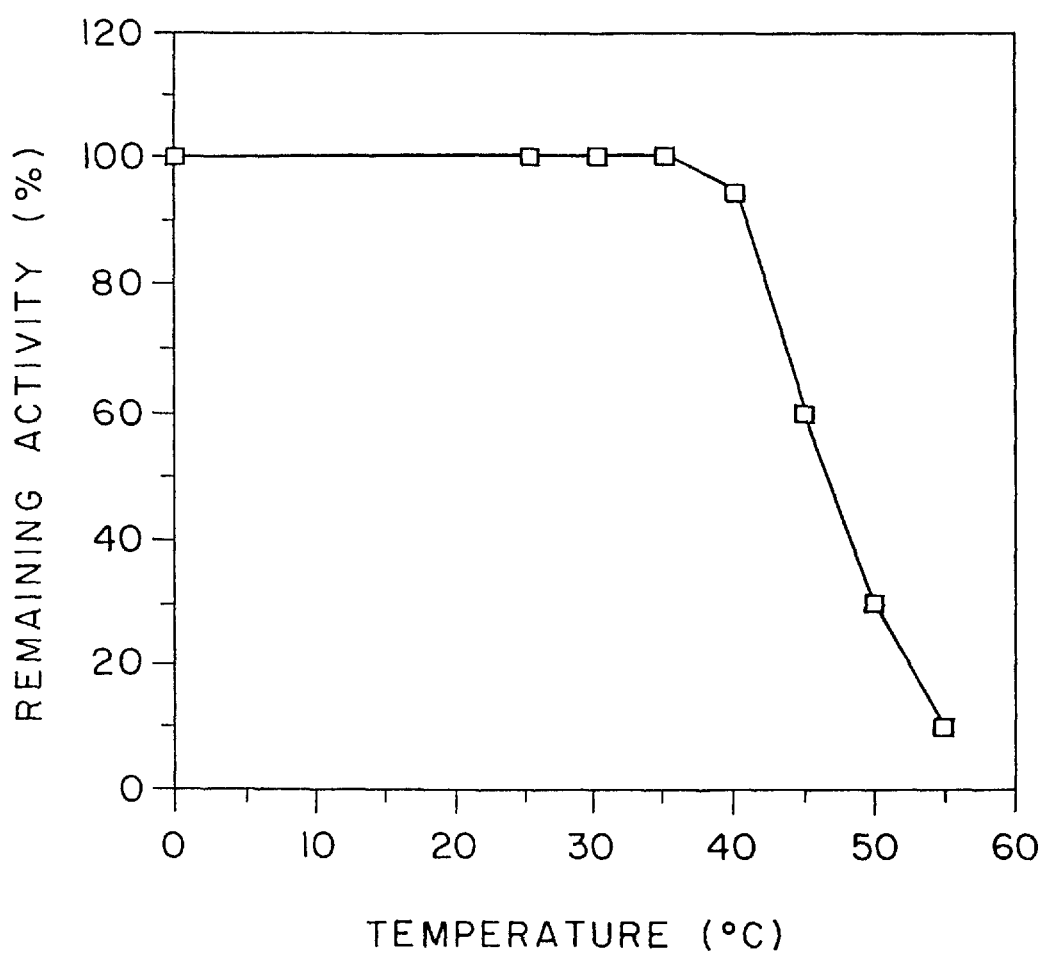
FIG. 8: Heat stability curve of sorbitol-6-phosphate dehydrogenase.

(9) Heat stability 100 mM Tris-HCl buffer solution (pH 8.5) of sorbitol-6-phosphate dehydrogenase 1 U/ml was heated for 10 minutes and remaining activity was measured according to the assay method hereinbefore. Results are shown in FIG. 8. Enzyme activity is stable at least up to 37° C.

(10) Effect of metal ion

Effect of 1 mM metal ions on sorbitol-6-phosphate dehydrogenase activity is shown in Table 4. Strong inhibition was observed in copper ion and lead ion.

TABLE 4

| Metal ion | Relateive activity |
| --- | --- |
| None | 100 |
| LiCl | 100 |
| NaCl | 100 |
| KCl | 100 |
| CsCl | 100 |
| CuCl$_2$ | 0 |
| BaCl$_2$ | 32 |
| ZnCl$_2$ | 6 |
| PbCl$_2$ | 2 |
| NiCl$_2$ | 100 |
| CoCl$_2$ | 100 |
| MnCl$_2$ | 40 |
| CaCl$_2$ | 100 |
| MgCl$_2$ | 100 |

Process for production of sorbitol-6-phosphate dehydrogenase are illustrated in detail.

Culture of Comamonas sp. SY-77-1

Each 100 ml of medium (pH 7.0) containing sorbitol 2.0% and brain heart infusion 2.0% in twenty 500 ml flask was sterilized at 120° C. for 20 minutes. A loopful culture of Comamonas sp. SY-77-1 was inoculated thereto and shake cultured at 28° C., 120 rpm, for 20 hours to obtain culture liquid 1.9 lit., enzyme activity 2.7 U/ml.

Isolation and Purification of Enzyme

The cultured liquid 1.9 lit. was centrifuged and the obtained microbial cells were washed with 20 mM Tris-HCl buffer solution (pH 8.5) 2 lit. Washed cells were suspended in the same buffer 50 ml and sonicated at 180 W for 30 minutes using ultrasonicator (INSONATOR 201M, Kubota Corp.) to obtain the lyzate. The lyzate was centrifuged at 12000 rpm for 20 minutes to obtain supernatant solution 42 ml (enzyme activity 105 U/ml, 4200 U). The supernatant solution was dialyzed using dialyzing tube against 20 mM Tris-HCl buffer solution (pH 8.0) 5 lit. at 5° C. for overnight to obtain crude enzyme solution 51 ml (enzyme activity 85 U/ml, 4340 U).

Enzyme solution was passed through a column of DEAE-Sepharose CL-6B (Pharmacia Inc.) 100 ml (2.6×19 cm) bufferized with 20 mM Tris-HCl buffer solution (pH 8.0). The column was washed with 20 mM Tris-HCl buffer solution (pH 8.0) 1 lit. containing 0.2M KCl then eluted with 20 mM Tris-HCl buffer solution (pH 8.0) 1 lit. containing 0.3M KCl to obtain enzyme solution 250 ml (enzyme activity 13 U/ml. 3250 U). NaCl was dissolved in the enzyme solution up to 3M. The enzyme solution was passed through a column of Phenyl-Sepharose (Pharmacia Inc.) 50 ml (1.5×28 cm) bufferized with 20 mM Tris-HCl buffer solution (pH 8.0) containing 3M NaCl.

Elution was performed by 3M–0M NaCl linear gradient. Fractions eluted at 1M–0M NaCl (enzyme activity 35 U/ml, 2450 U) were collected. Bovine serum albumin 100 mg was dissolved in the enzyme solution. The solution was lyophilized to obtain enzyme powder 68 mg (enzyme activity 33 U/ml).

Referential Example 2

Isolation of Chromosomal DNA

Erwinia sp. SK-472-20 (FERM BP-4492) was shake cultured in a medium (yeast extract 0.5%. peptone 0.5%, $K_2HPO_4$ 0.05%, $KH_2PO_4$ 0.05%. $NH_4Cl$ 0.05%, and $MgSO_4.7H_2O$ 0.03%, pH 7.0) 100 ml at 37° C. for 40 hours. The cultured mass was centrifuged by high speed freezing centrifuge (TomiiCX-250) at 6500 rpm (7660 G) for 10 minutes to collect microbial cells.

The cells were suspended in a solution 20 ml containing of 50 mM Tris-HCl buffer solution (pH 8.0), 50 mM EDTA (pH 8.0) and 15% sucrose. Lysozime (Seikagaku Kogyo K.K.) was added up to final concentration 2 mg/ml and treated at 37° C. for 10 minutes to lyzate cell wall.

10% sodium lauryl sulfate (SIGMA Corp.) solution 1 ml was added to the suspension and treated at 37° C. for 5 minutes. Chloroform/phenol (1:1) mixture 21 ml was added with stirring and the mixture was centrifuged at 10000 rpm (12080 G) for 10 minutes to collect water layer. Twice volume of ethanol was added gently to the water phase, slowly stirred using glass rodto twine DNA in the glass rod. DNA was dissolved in the solution 20 ml consisting of 10 mM Tris-HCl buffer solution (pH 8.0) and 1 mM EDTA. RNase (Pharmacia Inc.) was added up to the final concentration at 10 μg/ml and treated at 37° C. for 30 minutes. Equal volume of mixture of phenol/chloroform (1/1) was added and treated by the same way hereinabove to isolated water phase.

Twice volume of ethanol was added to the water phase and isolated the DNA by the same procedures hereinabove, then DNA was dissolved in a solution 2 ml consisting of 10 mM Tris-HCl buffer solution (pH 8.0) and 1 mM EDTA.

Referential Example 3

Preparation of Gene Library of Erwinia sp. SK-472-20

Chromosome of Erwinia sp. SK-472-20 5 μg obtained in referential example 2 was digested using restriction enzyme HindIII (Takara Shuzo Co.) 10 units in a solution containing 10 mM Tris-acetate buffer (pH 7.5), 50 mM NaCl, 10 mM $MgCl_2$ and 1 mM DTT at 37° C. for 2 hours.

Vector plasmid PUC118 (Takara Shuzo Co.) 3 μg in the other vessel was split by HindIII (Takara Shuzo Co.) 10 units in a solution containing 10 mM Tris-acetate buffer. (pH 7.5), 50 mM NaCl, 10 mM $MgCl_2$ and 1 mM DTT at 37° C. for 2 hours, and alkaline phosphatase (Takara Shuzo Co.) 1 unit was added thereto for dephosphorylation of 5'-terminal, then treated at 65° C. for 2 hours.

The thus obtained two DNA solutions hereinabove were mixed. Equal volume of phenol/chloroform (1/1) mixture was added to the mixture and centrifuged to separate water layer. A 1/10 volume of 3M sodiuim acetate solution and twice volume of ethanol were added to the water layer and centrifuged to collect DNA which was dried up in vacuo.

The obtained DNA was dissolved in a solution containing 10 mM Tris-HCl buffer (pH 8.0 and 1 mM EDTA solution and was ligated in the presence of 66 mM Tris-HCl buffer (pH 7.6), 6.6 mM $MgCl_2$, 10 mM DTT and 660 μM ATP (Boehringer Mannheim GmbH) using T4DNA ligase (Takara Shuzo Co.) 300 units at 4° C. for 16 hours.

The ligated DNA was transformed into competent cell [A. Nishimura et al. Nucleic Acid Res. 18, 6169 (1990)] of E.coli DH1 (ATCC 33849) [F-, recA1, endA1, gyrA96, thi-1, hsdR17 (fk-, mk+), supE44, relA1, λ-][Molecular Cloning: Cold Spring Harbor, 504–506 (1982)]. The transformed cells were incubated in BHI agar medium containing ampicillin 50 μg/ml at 37° C. for overnight to obtain about 10,000 transformants which were designated as gene library of Erwinia sp. SK-472-20.

Example 2

Preparation of Radioactive Oligonucleotide Probe

N-terminal amino acid sequence of purified authentic sample of sorbitol kinase is shwon in FIG. 13 (SEQ ID NO. 2). Amino acid sequences of lysylendopeptidase treated fragments are shown in FIG. 14 (SEQ ID NO. 3), FIG. 15 (SEQ ID NO. 4) and FIG. 16 (SEQ ID NO. 5).

Nucleotide sequence from 5'-terminal of the gene was estimated. Since estimated nucleotide sequence may be thought to be various combinations, oligonucleotides of small number of combinations were designed and experiments were conducted. The oligonucleotides were prepared by a method of R. L. Lessinger et al.(J. Am. Chem. Soc., 98: 365 5) using DNA synthesizer [Cyclon (Biosearch Inc.)]. In the N-teminal amino acid sequence in FIG. 13, synthetic DNA corresponding to amino acid sequence from amino acid residue No. 34 Asp to No. 39 Thr was prepared. 32 combinations will exist in case of 17 mer. 17 mer oligonucleotide probe SK1 shown in FIG. 17 ①, SEQ. ID NO. 6 which is complementary to mRNA estimated by amino acid sequence, was prepared.

Isotope $^{32}$P was incorporated into the thus obtained oligonucleotide 5 pmol in the presence of T4 polynucleotide kinase buffer [50 mM Tris-HCl buffer (pH 8.0), 10 mM $MgCl_2$, 4 mM DTT, 0.1 mM EDTA and 0.1 mM spermidine] and 370 kBq [γ-$^{32}$P] ATP (Amersham Inc.) by T4 polynucleotide kinase 8.5 units at 37° C. for 30 minutes to prepare radioactive oligonucleotide probe. However, although cloning of sorbitol kinase gene was attempted by using the radioactive oligonucleotide probe under various conditions, required gene could not be obtained.

In the N-teminal amino acid sequence in FIG. 13, synthetic DNA corresponding to amino acid sequence from amino acid residue No. 34 Asp to No. 40 Ile was prepared. 128 combinations will exist in case of 20 mer. Considering the frequency of use of codon in Erwinia gene [K. Wada et al. (Nucleic Acids Research, 20: 2114, 1992)], combination of codon for amino acid residue No. 39 Thr is selected to ACC and ACG. 20 mer oligonucleotide probe SK1 shown in FIG. 17 ②, SEQ. ID NO. 7 which is complementary to mRNA estimated by amino acid sequence, was prepared.

Isotope $^{32}$P was incorporated by the same way as described hereinabove to prepare radioactive oligonucleotide probe. However, although cloning of sorbitol kinase gene was attempted by using the radioactive oligonucleotide probe under various conditions, required gene could not be obtained. The reason was confirmed later that the selected codon for Thr in that sequence was very rare codon of ACT. This means that selection of the present gene is quite difficult.

In the N-teminal amino acid sequence underlined in FIG. 13, synthetic DNA corresponding to amino acid sequence from amino acid residue No. 34 Asp to No. 44 Ala was prepared. 9216 combinations will exist in case of 32 mer. Consequently, in the six amino acids, inosine was used in the third letter of codon and the combination was restricted within 16 combinations. 32 mer oligonucleotide probe SK3 shown in FIG. 17 ③, SEQ. ID NO. 8 which is complementary to mRNA estimated by amino acid sequence, was prepared.

Isotope $^{32}$P was incorporated by the same way as described hereinabove to prepare radioactive oligonucleotide probe.

Example 3

Screening for Sorbitol Kinase Gene Containing DNA

Nylon membrane filter (Magnagraphnylon, Microseparation Inc.) was overlayered on the ampicillin resistant colonies of the Erwinia sp. SK-472-20 gene DNA on the agar plate medium to transfer a part of the colonies on the filter. The filter was soaked in alkaline denaturant solution (0.5N—NaOH containing 1.5M NaCl) for 5 minutes, was further soaked in the neutralization solution [a mixture of 0.5M Tris-HCl buffer (pH 7.0) and 3M NaCl] for 5 minutes and dried.

The filter was heated at 80° C. for 2 hours to bind the plasmid DNA in the bacterial cells on the filter. The filter was further soaked in hybridization solution (NaCl 43.8 g/l, trisodiuim citrate 22.1 g/l, 50 mM triphosphate (pH 6.5), sodium lauryl sulfate 1 g/l, ficol 1 g/l, polyvinyl pyrrolidone 1 g/l, BSA 1 g/l, salmon sperm DNA 250 mg/l and formamide 200 ml/l) and conducted hybridization at 42° C. for 1 hour. The filter was again soaked into the new hybridization solution, and the radioactive oligonucleotide probe shown in FIG. 17 ③ obtained in the example 1 was added and was subjected to hybridization at 42° C. for one day.

After hybridization was completed, the filter was washed three times with washing solution (NaCl 4.38 g/l, trisodium citrate 2.21 g/l and sodium lauryl sulfate 1 g/l), then the filter was soaked in the washing solution at 42° C. for 10 minutes to remove excess probes. The filter was dried, overlayered on X-ray film (Fuji Photo Film Co., HR-H) and subjected to autoradiography in the dark at −80° C. for 24 hours.

Figure 11:
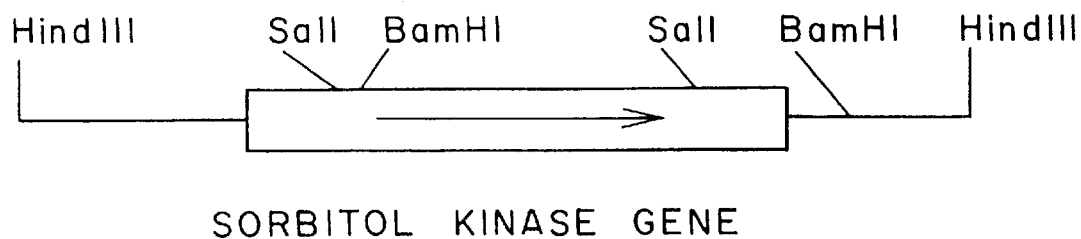
FIG. 11: Restriction map of chromosomal DNA orginated from Erwinia sp. SK-472-20 in plasmid pSK1.

The film was developed and the colonies showing positive signals were found. Restriction map of the DNA inserted in the plasmid in recombinant E.Coli which forms said colonies is shown in FIG. 11.

The said colony has been designated as E.coli DH1-pSK1 (FERM BP-4496) which is a transformant containing DNA coding sorbitol kinase. The plasmid in the said transformant E.coli DH1-pSK1 was designated as pSK1. Plasmid construction strategies for pSK1 is shown in FIG. 18.

Example 4

Determination of Nucleotide Sequence of DNA Coding Sorbitol Kinase

Figure 12:
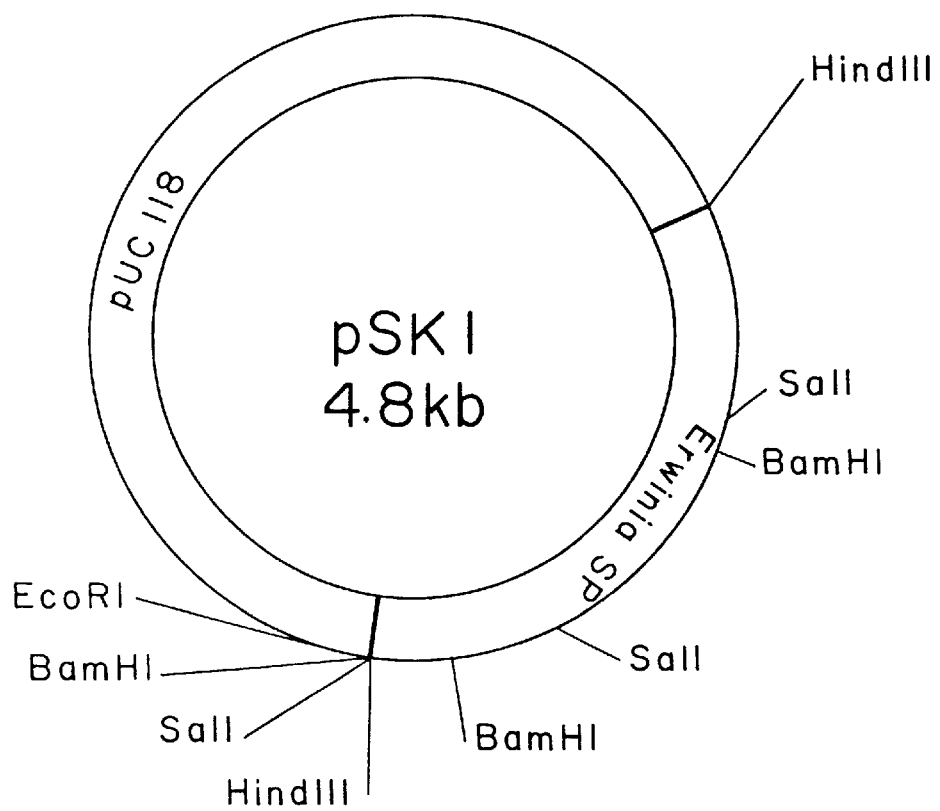
FIG. 12: Schematic drawing of structure of the plasmid pSK1.

The PSK1DNA was extracted from E.coli DH1 harboring plasmid pSK1 by a method of T. Malniatis et al. ["Molecular Cloning: Cold Spring Harbor", p. 86–94 (1982)]. Schematic drawing of this plasmid is shown in FIG. 12. A sequence originated from Erwinia sp. SK-472-20 chromosome was determined by dideoxy chain termination method (Science, 214: 1205–1210, 1981) to confirm whole DNA coding sorbitol kinase. The total nucleotide sequence thereof was determined and was confirmed at least to contain the sequence shown in FIG. 10.

N-terminal amino acid sequence of sorbitol kinase and lysylendopeptidase treated fragment were identified in the same frame.

Amino acid sequence of sorbitol kinase shown in FIG. 9 as well as its activity was also confirmed.

Example 5

Expression of Sorbitol Kinase Activity in E.coli

The transformant E.coli DH1-pSK harboring sorbitol kinase coding DNA obtained in the example 3 was cultured in BHI medium containing ampicillin 50 μg/ml at 37° C. for 24 hours, and cultured mass was centrifuged at 15,000 rpm for 1 minute to collect the precipitate. Equal amount of 10M Tris-HCl buffer (pH 8.0) was added to the precipitate and the mixture was sonicated. Activity of sorbitol kinase was assayed by the following methods.

A reaction mixture 1 ml consisting of 100 mM Tris-HCl buffer solution (pH 8.5), 2 mM ATP, 2 mM MgCl$_2$, 5 unit/ml sorbitol-6-phosphatedehydrogenase (refer to referential example 3), 1 mM NAD, 5 units/ml diaphorase (Asahi Chem. Ind. Co.), 0.025% nitrotetrazolium blue, 100 mMD-sorbitol and 0.1% Triton X-100 was incubated with the aliqluot diluted sonicated microbial cells 20 μl at 37° C. for 10 minutes. Reaction was stopped by adding 0.1N HCl 2.0 ml and the optical absorption at 550 nm was measured for determination of sorbitol kinase activity. For control study, sonicated E.coli DH1 harboring pUC118 was treated by the same way as above to determine activity of sorbitol kinase. Results showed very surprisingly that activity of transformant microbial cells harboring plasmid pSK1 was 200 U/ml, but the cells harboring plasmid pUC 118 was 0 U/ml. Accordingly, the transformant having sorbitol kinase activity was confirmed. Isolated and purified sorbitol kinase showed identical molecular weight and isoelectric point as of the enzyme of Erwinia sp. SK-472-20, consequently the physico-chemical properties of expressed protein was confirmed.

EFFECT OF THE INVENTION

The present invention provides sorbitol kinase and novel process for production of sorbitol kinase by microorganism belonging to genus Erwinia. The invention also provides enzyme for assaying sorbitol using the present enzyme. Further according to the present invention, a gene DNA expressing sorbitol kinase is screened from chromosomal DNA library originated from Erwinia sp. SK-472-20; a recombinant plasmid of expression vector constructed by using the said DNA was, for example transformed into a microorganism belonging to E.coli; and the thus obtained transformant microorganism produces sorbitol kinase having enzymatic action utilizing mainly ATP, but not substantially phosphoenolpyruvate, as the phosphate donor.

Furthermore according to the present invention, whole amino acid sequence of sorbitol kinase and nucleotide sequence of gene DNA coding the said amino acids. Protein engineering of the said enzyme such as converting the substrate and coenzyme specificities or improving heat resistance, can be attempted.

We claim:

1. An isolated and purified sorbitol kinase having at least the following physicochemical properties:
   (a) utilizing mainly ATP, but not substantially phosphoenolpyruvate, as the phosphate donor catalyzing a reaction of generating sorbitol-6-phosphate and ADP from sorbitol and ATP of the formula, sorbitol+ATP→sorbitol-6-phosphate+ADP (b) substrate specificity for sorbitol
   (c) N-terminal amino acid sequence containing (SEQ ID NO: 10)
   Met—Arg—Ile—Gly—Ile—Asp—Leu—Gly—Gly—
   —Thr—Lys—Thr—Glu—Val—Ile—Ala—Leu—Ser—Glu—Gln (d) heat stable at least up to 60° C. when a 100 mM Tris-HCl buffer (pH 8.5, containing 0.5 U/ml of sorbitol kinase) is heated for 15 minutes at various temperatures and the residual acitvity is measured.

2. The sorbitol kinase according to claim 1 which has the molecular weight: 35,000±5,000 as determined by SDS polyacrylamide gel electrophoresis.

3. The sorbitol kinase according to claim 2 which has the following physicochemical properties:
   (a) optimum pH of pH 8.5–9.5
   (b) pH stability in the range of pH 6.5–10.0
   (c) optimum temperature approximately at 50° C.

4. A process for production of the sorbitol kinase of claim 1 comprising culturing sorbitol kinase producing microorganism belonging to genus Erwinia in aculture medium and isolating said sorbitol kinase from the cultured mass.

5. The process according to claim 4 wherein sorbitol kinase producing microorganism belonging to genus Erwinia is Erwinia sp. SK-472-20 (FERM BP-4492).

6. An isolated and purified sorbitol kinase having the amino acid sequence of SEQ ID NO: 1.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
       ( A ) LENGTH: 1075 base pairs
       ( B ) TYPE: nucleic acid
       ( C ) STRANDEDNESS: double
       ( D ) TOPOLOGY: linear ( i i ) MOLECULE TYPE: DNA (genomic)

( i x ) FEATURE:
       ( A ) NAME/KEY: CDS
       ( B ) LOCATION: 31..972

( x i ) SEQUENCE DESCRIPTION: SEQ ID NO:1:

```
GTTGATAATC AAAATAATGA GGAGTGTCTT ATG CGT ATT GGG ATT GAT TTG GGC          54
                                   Met Arg Ile Gly Ile Asp Leu Gly
                                    1               5

GGC ACT AAA ACA GAA GTC ATC GCA CTG AGC GAG CAG GGG GAG CAA CTG         102
Gly Thr Lys Thr Glu Val Ile Ala Leu Ser Glu Gln Gly Glu Gln Leu
         10              15                  20

TTC CGC CAC CGT CTG CCT ACG CCG CGC GAT GAT TAT CAC CAG ACT ATC         150
Phe Arg His Arg Leu Pro Thr Pro Arg Asp Asp Tyr His Gln Thr Ile
 25              30                  35                  40

GAG ACG ATT GCC CGG CTG GTC GAC ATG GCT GAG CAG GCG ACA GGG CAG         198
Glu Thr Ile Ala Arg Leu Val Asp Met Ala Glu Gln Ala Thr Gly Gln
                 45                  50                  55

ACC GGC ACC GTT GGG ATG GGG ATC CCG GGG TCA ATC TCG CCC TAT ACC         246
Thr Gly Thr Val Gly Met Gly Ile Pro Gly Ser Ile Ser Pro Tyr Thr
                 60                  65                  70

GGG GTG GTT AAA AAC GCC AAC TCC ACC TGG CTC AAC GGT CAG CCT TTT         294
Gly Val Val Lys Asn Ala Asn Ser Thr Trp Leu Asn Gly Gln Pro Phe
             75                  80                  85

GAT AAA GAT TTA AGT CAG CGC CTG AAC CGG GAA GTG CGT CTG GCA AAT         342
Asp Lys Asp Leu Ser Gln Arg Leu Asn Arg Glu Val Arg Leu Ala Asn
         90                  95                 100

GAC GCC AAC TGT CTG GCC GTC TCC GAA GCC ATT GAC GGT GCC GCC GCA         390
Asp Ala Asn Cys Leu Ala Val Ser Glu Ala Ile Asp Gly Ala Ala Ala
105                 110                 115                 120

GGG GCC CAG ACC GTT TTT GCG GTC ATT ATC GGG ACC GGC TGT GGC GCA         438
Gly Ala Gln Thr Val Phe Ala Val Ile Ile Gly Thr Gly Cys Gly Ala
                125                 130                 135

GGC GTG GCC CTG GGC GGG CGT GCC CAT ATT GGC GGC AAC GGT ACG GCG         486
Gly Val Ala Leu Gly Gly Arg Ala His Ile Gly Gly Asn Gly Thr Ala
                140                 145                 150

GGC GAG TGG GGA CAT AAC CCC TTG CCG TGG ATG GAT GAA GAT GAA CTT         534
Gly Glu Trp Gly His Asn Pro Leu Pro Trp Met Asp Glu Asp Glu Leu
            155                 160                 165

AAA TAC CGC GCC GAG GTG CCG TGC TAT TGC GGC AAG CAG GGC TGT ATT         582
Lys Tyr Arg Ala Glu Val Pro Cys Tyr Cys Gly Lys Gln Gly Cys Ile
        170                 175                 180

GAG ACG TTT ATC TCC GGC ACC GGT TTT GCC ACC GAT TAC CAC CGC CTG         630
Glu Thr Phe Ile Ser Gly Thr Gly Phe Ala Thr Asp Tyr His Arg Leu
185                 190                 195                 200
```

```
AGT GGC CAG CCA CTC AAG GGG AAC GAG ATT ATG CGC CGG GTC GGG GAA         678
Ser Gly Gln Pro Leu Lys Gly Asn Glu Ile Met Arg Arg Val Gly Glu
            205                 210                 215

CAC GAT CCG GTG GCT GAG CTG GCT CTC AGC CGC TAT GAA ATG CGG CTG         726
His Asp Pro Val Ala Glu Leu Ala Leu Ser Arg Tyr Glu Met Arg Leu
            220                 225                 230

GCG AAA TCC CTG GCG CAC GTG GTG AAT ATC CTT GAC CCT GAC GTG ATT         774
Ala Lys Ser Leu Ala His Val Val Asn Ile Leu Asp Pro Asp Val Ile
            235                 240                 245

GTG CTC GGC GGC GGG ATG AGC AAC GTC GAC CGT TTA TAT GCC ACG GTA         822
Val Leu Gly Gly Gly Met Ser Asn Val Asp Arg Leu Tyr Ala Thr Val
            250                 255                 260

CCG AAT CTG GTG AAG CAG TGG GTC TTC GGG GGT GAG TGT GAA ACC CCG         870
Pro Asn Leu Val Lys Gln Trp Val Phe Gly Gly Glu Cys Glu Thr Pro
265                 270                 275                 280

ATC CGA AAG CGG TGC ACG GGG ACT CCA GCG GCG TGC GCG GCG CCG CGT         918
Ile Arg Lys Arg Cys Thr Gly Thr Pro Ala Ala Cys Ala Ala Pro Arg
            285                 290                 295

GGC TCT GGC CGC TAT AGC CAT TCT CCC TCT CCC TAC GTG AGA GGG GCG         966
Gly Ser Gly Arg Tyr Ser His Ser Pro Ser Pro Tyr Val Arg Gly Ala
            300                 305                 310

GGA TGA GGGTGCCTC ATGCAGGGCA CCCTCACTCC ACCGCAAACA CCTTATCCAG          1022
Gly *

CTTGCTATAC CCCAGCCCGT TAATCTTCTT CACTTTGATC TGCACCGGGA TCC             1075
```

( 2 ) INFORMATION FOR SEQ ID NO:2:

( i ) SEQUENCE CHARACTERISTICS:
        ( A ) LENGTH: 313 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Ile Gly Ile Asp Leu Gly Gly Thr Lys Thr Glu Val Ile Ala
 1               5                  10                  15

Leu Ser Glu Gln Gly Glu Gln Leu Phe Arg His Arg Leu Pro Thr Pro
            20                  25                  30

Arg Asp Asp Tyr His Gln Thr Ile Glu Thr Ile Ala Arg Leu Val Asp
            35                  40                  45

Met Ala Glu Gln Ala Thr Gly Gln Thr Gly Thr Val Gly Met Gly Ile
        50                  55                  60

Pro Gly Ser Ile Ser Pro Tyr Thr Gly Val Val Lys Asn Ala Asn Ser
65                  70                  75                  80

Thr Trp Leu Asn Gly Gln Pro Phe Asp Lys Asp Leu Ser Gln Arg Leu
                85                  90                  95

Asn Arg Glu Val Arg Leu Ala Asn Asp Ala Asn Cys Leu Ala Val Ser
            100                 105                 110

Glu Ala Ile Asp Gly Ala Ala Ala Gly Ala Gln Thr Val Phe Ala Val
            115                 120                 125

Ile Ile Gly Thr Gly Cys Gly Ala Gly Val Ala Leu Gly Gly Arg Ala
        130                 135                 140

His Ile Gly Gly Asn Gly Thr Ala Gly Glu Trp Gly His Asn Pro Leu
145                 150                 155                 160

Pro Trp Met Asp Glu Asp Glu Leu Lys Tyr Arg Ala Glu Val Pro Cys
                165                 170                 175

Tyr Cys Gly Lys Gln Gly Cys Ile Glu Thr Phe Ile Ser Gly Thr Gly
```

|     |     |     |     |     | 180 |     |     |     |     | 185 |     |     |     |     | 190 |     |
| --- | --- | --- | --- | --- | --- | --- | --- | --- | --- | --- | --- | --- | --- | --- | --- | --- |

Phe Ala Thr Asp Tyr His Arg Leu Ser Gly Gln Pro Lys Gly Asn
        195                         200                        205

Glu Ile Met Arg Arg Val Gly Glu His Asp Pro Val Ala Glu Leu Ala
210                        215                        220

Leu Ser Arg Tyr Glu Met Arg Leu Ala Lys Ser Leu Ala His Val Val
225                    230                235                240

Asn Ile Leu Asp Pro Asp Val Ile Val Leu Gly Gly Gly Met Ser Asn
                 245                    250                  255

Val Asp Arg Leu Tyr Ala Thr Val Pro Asn Leu Val Lys Gln Trp Val
           260                  265                270

Phe Gly Gly Glu Cys Glu Thr Pro Ile Arg Lys Arg Cys Thr Gly Thr
        275                 280                  285

Pro Ala Ala Cys Ala Ala Pro Arg Gly Ser Gly Arg Tyr Ser His Ser
   290                    295                    300

Pro Ser Pro Tyr Val Arg Gly Ala Gly
305                       310

( 2 ) INFORMATION FOR SEQ ID NO:3:

( i ) SEQUENCE CHARACTERISTICS:
        ( A ) LENGTH: 52 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

Met Arg Ile Gly Ile Asp Leu Gly Gly Thr Lys Thr Glu Val Ile Ala
1                 5                    10                 15

Leu Ser Glu Gln Gly Glu Gln Leu Phe Arg His Arg Leu Pro Thr Pro
           20                  25                   30

Arg Asp Asp Tyr His Gln Thr Ile Glu Thr Ile Ala Arg Leu Val Asp
                35                  40              45

Met Ala Glu Gln
      50

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:4:

Asn Ala Asn Ser Thr Trp Leu Asn Gly Gln Pro Phe Asp Lys
1                 5                    10

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:5:

```
        Xaa  Trp  Val  Phe  Gly  Gly  Glu  Xaa  Glu  Thr  Pro  Ile  Arg  Lys
        1              5                        10
```

( 2 ) INFORMATION FOR SEQ ID NO:6:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:6:

```
        Tyr  Arg  Ala  Glu  Val  Pro  Cys  Tyr  Cys  Gly  Lys  Gln  Gly  Cys  Ile  Glu
        1              5                        10                       15

Thr  Phe  Ile  Ser  Gly  Thr  Gly  Phe  Ala  Thr  Asp  Tyr  His  Arg  Leu  Ser
                       20                       25                       30
```

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

GAYGAYTAYC AYCARAC                                                      17

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

GAYGAYTAYC AYCARACSAT                                            20

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:9:

GAYGAYTAYC AYCANACNAT NGANACNATN GC                            32

( 2 ) INFORMATION FOR SEQ ID NO:10:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:10:

| Met | Arg | Ile | Gly | Ile | Asp | Leu | Gly | Gly | Thr | Lys | Thr | Glu | Val | Ile | Ala |
|---|---|---|---|---|---|---|---|---|---|---|---|---|---|---|---|
| 1 | | | | 5 | | | | | 10 | | | | | 15 | |

| Leu | Ser | Glu | Gln |
|---|---|---|---|
| | | | 20 |